(12) United States Patent
Brown et al.

(10) Patent No.: US 10,906,934 B2
(45) Date of Patent: Feb. 2, 2021

(54) PROTEIN PURIFICATION METHODS

(75) Inventors: Arick Brown, Pacifica, CA (US); Junyan Ji, South San Francisco, CA (US); Jun Liu, Pacifica, CA (US); Yuchang John Wang, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 568 days.

(21) Appl. No.: 14/007,610

(22) PCT Filed: Mar. 23, 2012

(86) PCT No.: PCT/US2012/030265
§ 371 (c)(1),
(2), (4) Date: May 7, 2014

(87) PCT Pub. No.: WO2012/134987
PCT Pub. Date: Oct. 4, 2012

(65) Prior Publication Data
US 2014/0309403 A1    Oct. 16, 2014

Related U.S. Application Data

(60) Provisional application No. 61/467,897, filed on Mar. 25, 2011.

(51) Int. Cl.
*C07K 1/34*     (2006.01)
*C12N 7/00*     (2006.01)
*C07K 16/00*    (2006.01)

(52) U.S. Cl.
CPC .............. *C07K 1/34* (2013.01); *C07K 16/00* (2013.01); *C12N 7/00* (2013.01); *C12N 2750/14351* (2013.01)

(58) Field of Classification Search
None
See application file for complete search history.

(56) References Cited

U.S. PATENT DOCUMENTS

| | | | |
|---|---|---|---|
| 4,618,533 A | 10/1986 | Steuck | |
| 4,816,567 A | 3/1989 | Cabilly et al. | |
| 5,096,637 A | 3/1992 | DiLeo et al. | |
| 5,591,828 A | 1/1997 | Bosslet et al. | |
| 5,629,084 A | 5/1997 | Moya | |
| 5,641,870 A | 6/1997 | Rinderknecht et al. | |
| 6,096,872 A | 1/2000 | Van Holten et al. | |
| 7,118,675 B2 * | 10/2006 | Siwak | B01D 61/142 210/638 |
| 7,238,785 B2 | 7/2007 | Govindan et al. | |
| 9,056,896 B2 * | 6/2015 | Hongo | C07K 1/34 |
| 2003/0230532 A1 * | 12/2003 | Rosenblatt | B01D 61/04 210/639 |
| 2004/0106184 A1 | 6/2004 | Senesac | |
| 2007/0059302 A1 * | 3/2007 | Baca | C07K 16/22 424/133.1 |
| 2009/0123989 A1 | 5/2009 | Weggeman | |
| 2010/0190965 A1 | 7/2010 | Yamaguchi et al. | |
| 2011/0034674 A1 | 2/2011 | Mehta | |

FOREIGN PATENT DOCUMENTS

| | | | |
|---|---|---|---|
| CN | 10150951 A | 4/2008 | |
| CN | 101262884 A | 9/2008 | |
| CN | 101155915 A | 8/2009 | |
| EP | 0 404 097 B1 | 6/1990 | |
| EP | 1 661 914 A1 | 5/2006 | |
| EP | 1 661 914 B1 | 5/2006 | |
| JP | WO 0213859 A1 * | 2/2002 | ....... A61K 39/39591 |
| WO | WO-93/11161 A1 | 6/1993 | |
| WO | 199810856 A1 | 3/1998 | |
| WO | WO-99/019343 A1 | 4/1999 | |
| WO | WO2003039485 A2 | 5/2003 | |
| WO | WO-2004001007 A2 * | 12/2003 | ........... A61K 9/0019 |
| WO | WO2005054275 A2 | 6/2005 | |
| WO | 2006083689 A2 | 8/2006 | |
| WO | 2006083689 A3 | 10/2006 | |
| WO | 2006108707 A1 | 10/2006 | |
| WO | 2008017338 A2 | 2/2008 | |
| WO | 2008017338 A3 | 5/2008 | |
| WO | WO2012134987 A1 | 10/2012 | |

OTHER PUBLICATIONS

Bolton et al., "Achieving high mass-throughput of therapeutic proteins through parvovirus retentive filters" *Biotechnology Progress* 26(6):1671-1677 (Nov. 2010, e-pub. Sep. 21, 2010).
Chen et al., "The use of anionic surfactants for reducing fouling of ultrafiltration membranes: their effects and optimization" *J. Membrane Sci.* 67(2-3):249-261 (Mar. 20, 1992).
Clackson et al., "Making antibody fragments using phage display libraries" *Nature* 352(6336):624-628 (Aug. 15, 1991).
Fane et al., "The effect of surfactant pretreatment on the ultrafiltration of proteins" *Desalination* 53(1-3):37-55 (1985).
Holliger et al., "Diabodies": Small bivalent and bispecific antibody fragments, *Proc. Natl. Acad. Sci. USA* 90:6444-6448 (Jul. 1993).
International Search Report dated Jul. 3, 2012, for PCT Application No. PCT/US12/30265, filed on Mar. 23, 2012, 1 page.

(Continued)

*Primary Examiner* — Daniel E Kolker
*Assistant Examiner* — James L Rogers
(74) *Attorney, Agent, or Firm* — Morrison & Foerster LLP

(57) ABSTRACT

The invention provides methods of reducing fouling of ultrafiltration membranes in processes wherein virus particles are removed from aqueous solutions comprising virus particles and at least one protein by adding a surfactant or non-surfactant, non-ionic agent to the aqueous solution prior to filtration. The invention also provides methods to dissociate protein aggregates or to reduce the formation of protein aggregates by adding a surfactant or non-surfactant, non-ionic agent to the protein solution.

62 Claims, 12 Drawing Sheets

(56) References Cited

OTHER PUBLICATIONS

Jones et al., "Replacing the complementarity-determining regions in a human Antibody with those from a Mouse" *Nature* 321(6069):522-525 (May 29, 1986).

Jonsson et al., "The influence of nonionic and ionic surfactants on hydrophobic and hydrophilic ultrafiltration membranes" *J. Membrane Sci.* 56(1):49-76 (Feb. 1, 1991).

Kohler and Milstein, "Continuous cultures of fused cells secreting antibody of predefined specificity" *Nature* 256:495-497 (Aug. 7, 1975).

Marks et al., "By-passing immunization, human antibodies from V-gene libraries displayed on phage" *J Mol. Biol.* 222:581-597 (1991).

Morrison et al., "Chimeric human antibody molecules: Mouse antigen-binding domains with human constant region domains" *Proc. Natl. Acad. Sci. USA* 81:6851-6855 (Nov. 1984).

Presta, "Antibody Engineering" *Curr. Opin. Struc. Biol.* 2:593-596 (1992).

Riechmann et al., "Reshaping human antibodies for therapy" *Nature* 332:323-327 (Mar. 1988).

Strauss et al., "Anion exchange chromatography provides a robust, predictable process to ensure viral safety of biotechnology products" *Biotechnology and Bioengineering* 102(1):168-175 (Jan. 1, 2009).

Written Opinion dated Jul. 3, 2012, for PCT Application No. PCT/US12/30265, filed on Mar. 23, 2012, 4 pages.

Zapata et al., "Engineering linear F(ab')₂ fragments for efficient production in *Escherichia coli* and enhanced antiproliferative activity" *Protein Eng.* 8(10):1057-1062 (1995).

Zhan et al., "Detection of Minute Virus of Mice Using Real Time Quantitative PCR in Assessment of Virus Clearance During the Purification of Mammalian Cell Substrate Derived Biotherapeutics" *Biologicals* 30(4):259-270 (Dec. 2002).

Brown, A. (Jul. 1, 2010, e-pub. Mar. 12, 2010). "Increasing Parvovirus Filter Throughput of Monoclonal Antibodies Using Ion Exchange Membrane Adsorptive Pre-filtration," *Biotechnology and Bioengineering*, 106(4):627-637.

European Notice of Opposition for European Patent Application No. 12763521.7, dated Apr. 8, 2019, Proprietor, F. Hoffmann-La Roche AG, Opponent Maiwald Patentanwalts—und Rchtsanwaltsgesellsfaft mbH, 24 pages total.

European Notice of Reply of the Patent Proprietor to the Notice of Opposition dated Aug. 15, 2019, for European Patent Application No. 12763521.7, Proprietor, F. Hoffmann-La Roche AG, Opponent Maiwald Patentanwalts—und Rchtsanwaltsgesellsfaft mbH, 20 pages.

European Notice of Reply to Proprietor's Response Letter regarding Opposition dated Sep. 26, 2019, for European Patent Application No. 12763521.7, Proprietor, F. Hoffmann-La Roche AG, Opponent Maiwald Jatentanwalts—und Rchtsanwaltsgesellsfaft mbH, 9 pages.

Millipore. (May 2008). "Millipore Product Selection Guide on Ultrafiltration Membranes. Ultrafiltration Membranes for Macromolecule Processing," Millipore 5 pages.

\* cited by examiner

PROTEIN PURIFICATION METHODS

CROSS-REFERENCE TO RELATED APPLICATIONS

This application is a National Phase filing under 35 U.S.C. § 371 of International Application No. PCT/US2012/030265 having an international filing date of Mar. 23, 2012; which claims priority to U.S. Provisional Application Ser. No. 61/467,897, filed on Mar. 25, 2011, each of which is hereby incorporated by reference in its entirety.

FIELD OF THE INVENTION

The current invention relates to the field of protein purification. More specifically, the present invention provides novel methods for reducing protein-induced fouling of ultrafiltration membrane filters in biologic drug manufacturing processes.

BACKGROUND OF THE INVENTION

Viruses are a potential contaminant in biologic drug manufacturing processes, particularly in cases where polypeptide-based drugs are derived from mammalian cell cultures or from whole organisms. In many cases, chemical or physical methods exist to inactivate viral contaminants but these methods are not generic to all viruses and in some cases, may impact activity of the biological drug. Parvoviruses provide a particular challenge to remove based on their general resistance to chemical and physical inactivating agents.

Current approaches to the prevention of parvoviral contamination of biological drugs include the use of membrane filtration of biological feed streams during the manufacturing process. Parvovirus particles are small; for example, some parvoviruses are as small as 23 nm. As such, parvovirus filters typically have an average pore size of 20 nm. Due to the small pore size, these filters are extremely sensitive to proteinaceous fouling resulting in frequent replacement of filters during the manufacturing process which contributes significantly to the cost of processing. Methods to reduce protein fouling of small pore filters include the use of prefilter such as an ion exchange filter (U.S. Pat. No. 7,118,675; Bolton, G R et al. 2010 *Biotechnol. Prog.*) or pre-treating the membrane filter with a non-ionic surfactant (Fane, A G et al. 1985 *Desalination* 53:37-55; Jonsson, A S, and Jonsson, B, 1991 *J. Membrane Sci.* 56:49-76; Chen, V. et al. 1992 *J. Membrane Sci.* 67:249-261). Results obtained with these approaches, however, have proven to be inconsistent, unpredictable and may be ineffective and/or cost prohibitive.

In addition to viral removal, membrane filters may be used to remove protein aggregates from biologic drugs. For example, aqueous solutions of antibodies may contain aggregates of antibodies that should be removed prior to administration to a patient to avoid potential toxic responses. These protein aggregates contribute to membrane filter fouling as well as reducing overall yields of the biologic drug.

Thus, there is a continuing need for better, more economical methods for filtration of biologic solutions to remove potential viral contaminants and reduce protein aggregates. The invention provided herein addresses these needs and provides additional benefits.

All references cited herein, including patent applications and publications, are incorporated by reference in their entirety.

BRIEF SUMMARY OF THE INVENTION

The present invention provides methods of reducing fouling of ultrafiltration membranes in processes where virus particles are removed from aqueous solutions of protein by adding a surfactant or non-surfactant, non-ionic agent directly to an aqueous protein feedstream prior to ultrafiltration. The methods provide the advantages of enhancing the mass throughput of the ultrafiltration membrane and increasing the lifespan of the ultrafiltration membrane. In addition, the invention provides methods to reduce or prevent the formation of aggregates in aqueous solutions of protein.

In one aspect, the invention provides methods of reducing fouling of an ultrafiltration membrane in a process wherein virus particles are removed from an aqueous solution comprising virus particles and at least one protein, the method comprising the steps of a) adding to said aqueous solution a surfactant or a non-surfactant, non-ionic agent selected from the group consisting of a polyethylene glycol, a cellulose derivative, arginine, and a dextran, and b) filtering said aqueous solution comprising said surfactant or said non-surfactant, non-ionic agent through said ultrafiltration membranes, wherein the presence of said surfactant or said non-surfactant, non-ionic agent in said aqueous solution reduces fouling of said ultrafiltration membrane.

In another aspect, the invention provides methods of enhancing filtration throughput efficiency of an ultrafiltration membrane in a process wherein virus particles are removed from an aqueous solution comprising virus particles and at least one protein, the method comprising adding a surfactant or a non-surfactant, non-ionic agent selected from the group consisting of a polyethylene glycol, a cellulose derivative, arginine, and a dextran to said aqueous solution before filtering said aqueous solution through said ultrafiltration membranes, wherein the presence of said surfactant or said non-surfactant, non-ionic agent in said aqueous solution enhances the filtration throughput efficiency of said ultrafiltration membrane as compared to in the absence of said surfactant or non-surfactant, non-ionic agent.

In one aspect, the invention provides methods to dissociate polypeptide aggregates or reduce the formation of polypeptide aggregates in an ultrafiltration feed stream comprising an aqueous solution comprising at least one protein, the method comprising adding a surfactant or a non-surfactant, non-ionic agent selected from the group consisting of a polyethylene glycol, a cellulose derivative, arginine and a dextran to said aqueous solution. In some embodiments, the method further includes an ultrafiltration step.

In one aspect, the invention provides methods of reducing fouling of an ultrafiltration membrane in a process wherein virus particles are removed from an aqueous solution comprising said virus particles and at least one protein, the method comprising the steps of a) filtering said aqueous solution through a device selected from the group consisting of one or more layers of adsorptive depth filters and one or more layers of charged or surface modified microporous membranes; b) adding a surfactant or non-surfactant, non-ionic agent selected from the group consisting of a polyethylene glycol, a cellulose derivative, arginine and a dextran to said aqueous solution; and c) filtering said aqueous solution comprising said surfactant or said non-surfactant, non-ionic agent through said ultrafiltration membranes, wherein the presence of said surfactant or said non-surfactant, non-ionic agent in said aqueous solution reduces fouling of said ultrafiltration membrane.

In another aspect, the invention provides methods of reducing fouling of an ultrafiltration membrane in a process wherein virus particles are removed from an aqueous solution comprising said virus particles and at least one protein, the method comprising the steps of a) adding a surfactant or non-surfactant, non-ionic agent selected from the group consisting of a polyethylene glycol, a cellulose derivative, arginine and a dextran to said aqueous solution, b) filtering said aqueous solution through a device selected from the group consisting of one or more layers of adsorptive depth filters and one or more layers of charged or surface modified microporous membranes; and c) filtering said aqueous solution comprising said surfactant or said non-surfactant, non-ionic agent through said ultrafiltration membranes, wherein the presence of said surfactant or said non-surfactant, non-ionic agent in said aqueous solution reduces fouling of said ultrafiltration membrane.

In some embodiments of any of the aspects of the invention outlined above, the surfactant is a non-ionic surfactant. Examples of non-ionic surfactants include, but are not limited to polysorbate 20, Triton® X-100, Triton® X-405, lauromacrogol, and polysorbate 80. In some embodiments of any of the aspects of the invention outlined above, the non-ionic surfactant is polysorbate 20.

In some embodiments of any of the aspects of the invention outlined above, the surfactant or non-surfactant, non-ionic agent is added to the aqueous solution at a concentration of 1-10,000 PPM. In some embodiments, the surfactant or non-surfactant, non-ionic agent is added to the aqueous solution at a concentration of 10-200 PPM.

In some embodiments of any of the aspects of the invention outlined above, the ultrafiltration membrane is a parvovirus retentive membrane. In some embodiments, the ultrafiltration membrane has a pore size of less than about 100 nm or less. In some embodiments, the ultrafiltration membrane has a pore size of about 20 nm or less. In some embodiments, the step of filtering the aqueous solution is by normal flow filtration.

In some embodiments of any of the aspects of the invention outlined above, the protein in the aqueous solution is an antibody. In some embodiments, the antibody is a monoclonal or humanized antibody.

In some embodiments of any of the aspects of the invention outlined above, addition of the surfactant or said non-surfactant, non-ionic agent to said aqueous solution enhances the filtration throughput efficiency of said ultrafiltration membrane by at least 10%. In some embodiments, the addition of the surfactant or the non-surfactant, non-ionic agent to the aqueous solution enhances the filtration throughput efficiency of said ultrafiltration membrane by at least 50%.

In some embodiments of any of the aspects of the invention outlined above, the virus particles are parvovirus particles.

The throughput of the ultrafiltration membrane (VF) in g/m² is plotted against the transmembrane pressure in pounds per square inch.

Figure 10:
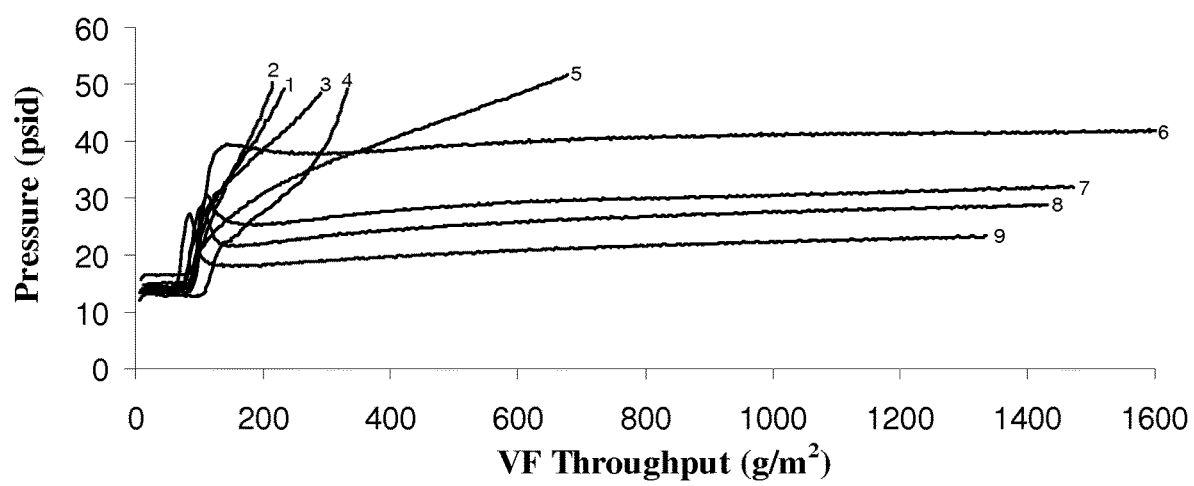

FIG. 10 shows the effect of various surfactants or non-surfactant, non-ionic agents on ultrafiltration of an aqueous solution comprising an anti-PDL1 antibody. The following were investigated, no additive (1), 1000 ppm octylβ-D-glucopyranoside (2), 1000 ppm PEG6000 (3), prefiltration using a Mustang S® cation exchange prefilter (4), 200 mM L-arginine HCl (5), 1000 ppm Triton® X-405 (6), 1000 ppm lauromacrogol (Brij® 35) (7), 1000 ppm polysorbate 20 (8), or 1000 ppm Triton® X-100 (9). The throughput of the ultrafiltration membrane (VF) in g/m² is plotted against the transmembrane pressure in pounds per square inch.

Figure 11:
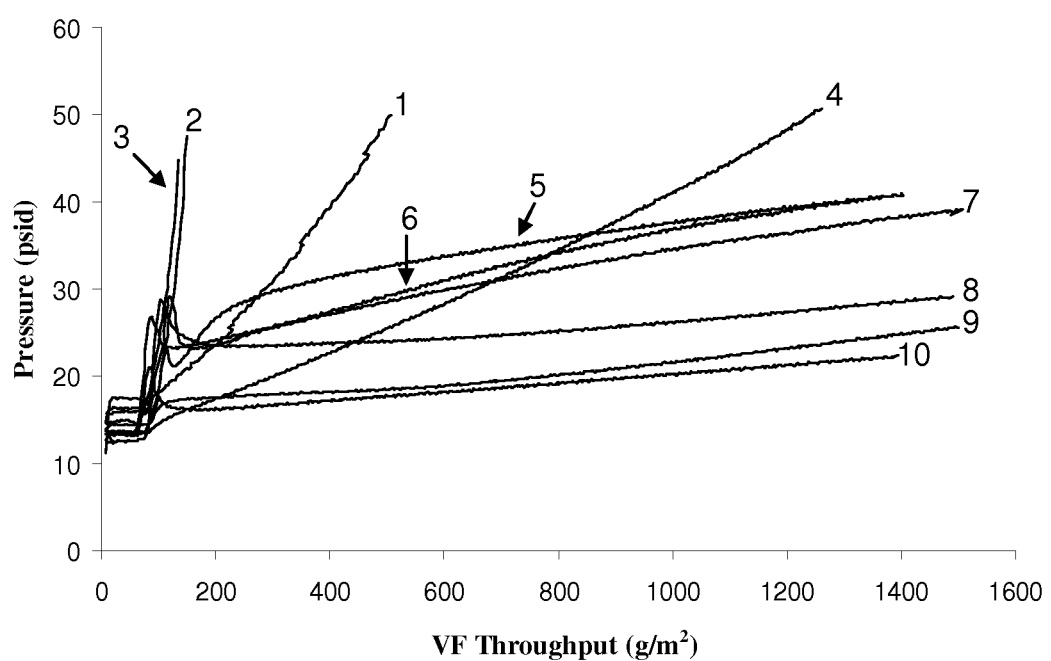

FIG. 11 shows the effect of various surfactants or non-surfactant, non-ionic agents on ultrafiltration of an aqueous solution comprising an anti-VEGF antibody. The following were investigated, no additive (1), 1000 ppm PEG8 stearate (2), 1000 ppm dextran LMW PEG 6000 (3), 1000 ppm PEG20 sorbitan (4), 1000 ppm PEG8 laurate (5), 1000 ppm polysorbate 80 (6), 1000 ppm polysorbate 20 (7), 1000 ppm lauromacrogol (Brij35) (8), prefiltration using a Mustang S® cation exchange prefilter (9), or 1000 ppm Triton® X-100 (10). The throughput of the ultrafiltration membrane (VF) in g/m² is plotted against the transmembrane pressure in pounds per square inch.

Figure 12:
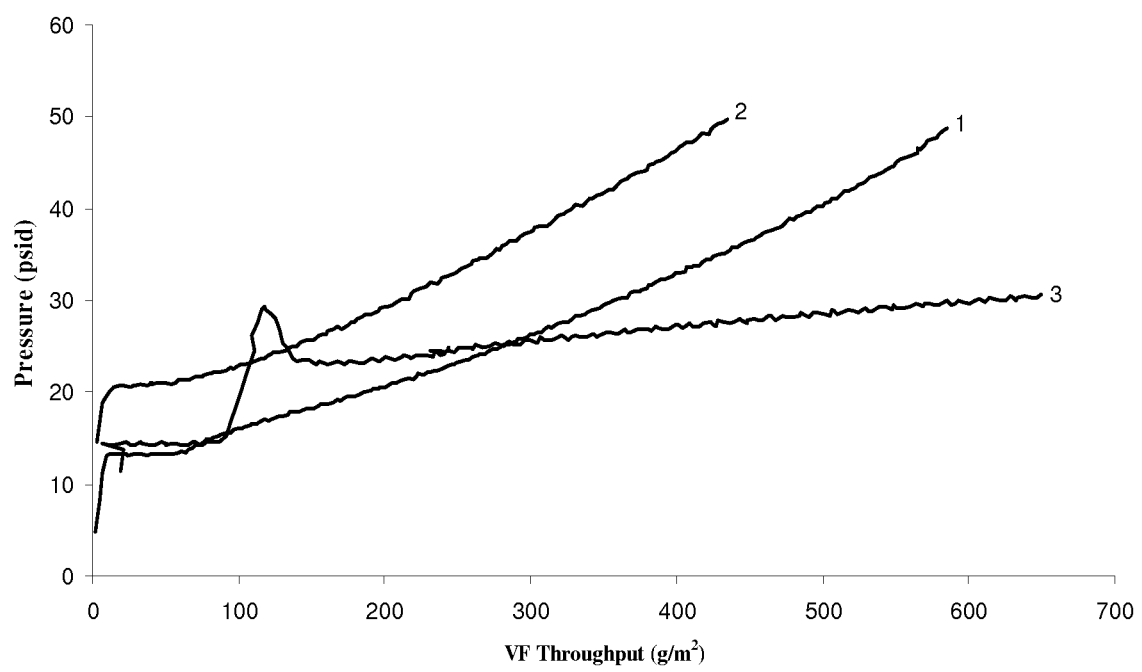

FIG. 12 shows the effect of pretreatment of an ultrafiltration membrane with polysorbate 20 prior to ultrafiltration of an aqueous solution of anti-VEGF antibody. In one sample the ultrafiltration membrane was pretreated with polysorbate 20 but no surfactant was added directly to the aqueous feedstock (2). In another sample, 1000 ppm polysorbate 20 was added directly to the aqueous feedstock but the ultrafiltration membrane was not pretreated with the surfactant (3). In a control sample, surfactant was not added directly to the feed stream and the parvovirus filter was not pretreated with surfactant (1). The throughput of the ultrafiltration membrane (VF) in g/m² is plotted versus the transmembrane pressure in pounds per square inch.

DETAILED DESCRIPTION OF THE INVENTION

The present invention provides methods of reducing fouling of ultrafiltration membranes in processes where viruses are removed from aqueous solutions comprising virus particles and at least one protein by adding a surfactant or certain non-surfactant, non-ionic agents to the aqueous solution prior to filtering the aqueous solution through an ultrafiltration membrane. The inventors have made the unexpected discovery that adding a surfactant or certain non-surfactant, non-ionic agents directly to the aqueous solution reduces fouling of ultrafiltration membranes to a greater extent compared to methods where ultrafiltration membranes are pre-treated with a surfactant prior to filtration. This reduction in fouling of ultrafiltration membranes can be achieved with a variety of surfactants; for example but not limited to polysorbate 20 and Triton® X-100, or non-surfactant, non-ionic agents; for example but not limited to polyethylene glycols, dextrans, arginine, or certain methyl- or ethyl-celluloses. In some embodiments, the invention provides methods of increasing throughput of ultrafiltration membranes in a process by which viral particles are removed from an aqueous feed stream by adding a surfactant or certain non-surfactant, non-ionic agent directly to the feed stream. In some embodiments, the invention provides methods of increasing the half-life of an ultrafiltration membrane in a process by which viral particles are removed from an aqueous feed stream by adding a surfactant or certain non-surfactant, non-ionic agent directly to the feed stream.

In some aspects of the invention, a surfactant or certain non-surfactant, non-ionic agent is added to the aqueous solution comprising virus particles and at least one protein in a system where the aqueous solution is passed through a pre-filter prior to ultrafiltration. In some embodiments, a surfactant or certain non-surfactant, non-ionic agent is added to the aqueous solution prior to passage through the pre-filter. In some embodiments, a surfactant or certain non-surfactant, non-ionic agent is added to the aqueous solution after passage through a pre-filter but prior to ultrafiltration.

In another aspect, the present invention provides methods to dissociate protein or polypeptide aggregates in ultrafiltration feed streams by adding a surfactant or certain non-surfactant, non-ionic agent to the aqueous solution prior to an ultrafiltration step. In another aspect, the present invention provides methods to reduce the formation of protein or polypeptide aggregates in ultrafiltration feed streams by adding a surfactant or certain non-surfactant, non-ionic agents to the aqueous solution prior to an ultrafiltration step. In some embodiments, the aqueous solution is passed through a prefilter prior to ultrafiltration.

Definitions

Unless defined otherwise, the meanings of all technical and scientific terms used herein are those commonly understood by one of skill in the art to which this invention belongs. Singleton, et al., Dictionary of Microbiology and Molecular Biology, 3rd ed., John Wiley and Sons, New York (2002), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

"Ultrafiltration" is a form of membrane filtration in which hydrostatic pressure forces a liquid against a semipermeable membrane. Suspended solids and solutes of high molecular weight are retained, while water and low molecular weight solutes pass through the membrane. In some examples, ultrafiltration membranes have pore sizes in the range of 1 to 100 nm. The terms "ultrafiltration membrane" and "ultrafiltration filter" may be used interchangeably.

A "virus retentive filter", "virus filter", "virus membrane", or "virus retentive membrane" is a type of ultrafiltration filter/membrane used for size-based removal of viruses from aqueous solutions containing virus particles. In particular, a virus retentive membrane has a pore size sufficient to retain the virus of interest, while still allowing the monomeric protein to pass through.

A "parvovirus retentive filter", "parvovirus filter", "parvovirus membrane", or "parvovirus retentive membrane" is a type of ultrafiltration filter/membrane used for size-based removal of parvoviruses from aqueous solutions containing parvovirus particles. In particular, a parvovirus retentive membrane has a small pore size; for example, in some cases, 20 nm, to remove small viral particles such as parvovirus particles which can be as small as 23 nm in diameter.

A "surfactant" or "surface active agent" is a compound, typically (but not necessarily) an organic compound, that contains both hydrophobic and hydrophilic groups, and is thus semi-soluble in both organic and aqueous solvents. Surfactants can be non-ionic, cationic or anionic.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

The term "antibody" or "antibodies" is used in the broadest sense and specifically covers, for example, single monoclonal antibodies (including agonist, antagonist, and neutralizing antibodies), antibody compositions with polyepitopic specificity, polyclonal antibodies, single chain antibodies, immunoadhesins, and fragments of antibodies as long as they exhibit the desired biological or immunological activity. The term "immunoglobulin" (Ig) is used interchangeable with antibody herein.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222: 581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

As used herein, the term "monomer(s)" refers to a single unit of a polypeptide or protein. For example, in the case of an antibody, a monomer consists of two heavy chains and two light chains; in the case of a one-armed antibody, a monomer consists of one heavy chain and one light chain.

As used herein, the term "aggregate(s)" refers to any multimers of a polypeptide or a polypeptide fragment. For example, an aggregate can be a dimer, trimer, tetramer, or a multimer greater than a tetramer, etc.

As used herein, the term "virus filter foulant" refers to any large molecular weight particle or high molecular weight species (HMWS) with a hydrodynamic diameter similar to or greater than the pore size distribution of an ultrafiltration membrane. Virus filter foulants include, but are not limited to, soluble high molecular weight polypeptide or protein aggregates, and soluble and/or insoluble aggregates of host cell impurities (e.g., CHOP).

The term "transmembrane pressure" refers to the differential applied pressure from the feed to the filtrate side of the membrane calculated by TMP [bar]=$P_F$-$P_f$, where $P_F$ is the feed pressure, $P_f$ is the retentate pressure, and $P_f$ is the filtrate pressure.

The term "enhancing the filtration throughput efficiency", and the like, when used in reference to an ultrafiltration membrane refers to the beneficial effect of increased volume throughput through an ultrafiltration membrane caused by addition of a surfactant or certain non-surfactant, non-ionic agents to a protein-containing aqueous solution prior to filtration of that aqueous solution through the ultrafiltration membrane.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments Ultrafiltration Membranes The present invention provides methods of reducing the fouling of ultrafiltration membranes in processes where viral particles are removed from an aqueous solution comprising viral particles and at least one protein. Prior to ultrafiltration, one or more surfactants or non-surfactant, non-ionic agents are added to the aqueous solution. The aqueous solution is then passed through the ultrafiltration membrane such that viral particles are retained by the ultrafiltration membrane and the one or more proteins pass through the membrane. For example, this process may be use in industrial scale production of protein and polypeptide therapeutics. A surfactant or non-surfactant, non-ionic agent is added to the protein feed stream prior to ultrafiltration of the feed stream to reduce filter fouling during processes to remove any virus particles that may be in the protein feed stream.

Ultrafiltration membranes may be formed from regenerated cellulose, polyethersulfone, polyarylsulphones, polysulfone, polyimide, polyamide, polyvinylidenedifluoride (PVDF) or the like. Representative ultrafiltration membranes include, but are not limited to Viresolve® membranes, Viresolve® Pro membranes, Viresolve® 180 membranes, Viresolve® 70 membranes, Viresolve® NFP membranes, Viresolve® NFR membranes, Retropore™ membranes, Virosart CPV membranes, Planova 75 membranes, Planova 35 membranes, Planova 20 membranes, Planova 15N membranes, VAG 300 membranes, Ultipor DVD membranes, Ultipor DV50 membranes, Ultipor DV20 membranes, and DVD Zeta Plus VR™ filters. In some embodiments, the ultrafiltration membrane is capable of removing parvovirus particles. In some embodiments, the ultrafiltration membrane is a parvovirus retention membrane.

The pore size of the ultrafiltration membranes should be small enough to retain undesirable virus particles while allowing the one or more proteins in the aqueous solution to pass through the membrane. In some embodiments of the invention, the pore size of the ultrafiltration membrane is less than 10 nm, 10 nm, 20 nm, 30 nm, 40 nm, 50 nm, 60 nm, 70 nm, 80 nm, 90 nm, 100 nm, 125 nm, 150 nm, 175 nm or 200 nm. In some embodiments, the pore size of the ultrafiltration membrane is 20 nm or less.

Ultrafiltration membranes may be characterized by a molecular weight cut off which represents the average molecular weight of a smallest protein that is retained by the ultrafiltration membrane. For example, most globular proteins with a molecular weight greater than 1000 kD will be retained by an ultrafiltration membrane with a molecular weight cut off of 1000 kD at a rate of 80-90% whereas most globular proteins with a molecular weight less than 1000 kD will pass through the ultrafiltration membrane. In some embodiments of the invention, the molecular weight cut off of the ultrafiltration membrane is between 200 kD and 1000 kD. In some embodiments of the inventions, the ultrafiltration membrane has a molecular weight cut off of 200 kD, 300 kD, 400 kD, 500 kD, 600 kD, 700 kD, 900 kD, or 1000 kD.

Filtration can be effected with one or more ultrafiltration membranes either by dead end (normal) flow filtration (NFF) or by tangential flow filtration (TFF). In NFF the feed stream is passed through a membrane and the large molecular weight substances are trapped in the filter while the filtrate is released at the other end. In TFF the majority of the feed flow travels tangentially across the surface of the filter, rather than into the filter. As such, the filter cake is substantially washed away during the filtration process, increasing the length of time that a filter unit can be operational. Ultrafiltration membranes for either mode of filtration can be supplied in either a cartridge (NFF) form, such as VIRESOLVE® NFP viral filters, or as cassettes (for TFF), such as PELLICON® cassettes. In a preferred embodiment, filtration is normal flow filtration.

More than one ultrafiltration membrane may be used in the processes of the invention. In some embodiments, the more than one ultrafiltration membranes are contacted with the aqueous solution in parallel.

The ultrafiltration membranes utilized in the process of this invention are characterized by a log retention value (LRV; the negative logarithm of the sieving coefficient) for virus particles and other, particles that increase monotomically with the diameter of the particle; in the size range of interest for virus of from about 1 nm to about 100 nm diameter. Empirically, the LRV increases continuously with the size of the particle projected area (the square of the particle diameter). Where one is concerned with removing small sized virus particles from protein solution; for example parvoviruses, satisfactory LRV of at least about 3 are obtained. However, the molecular weight cutoff is reduced thereby reducing protein recovery. One skilled in the art may choose a membrane that gives satisfactory LRV and protein recovery. Log reduction values for virus particles (single solutes in solution; in absence of protein) depend upon the virus particle size. For example, an LRV of greater than about 3 may be obtained with small sized virus such as parvovirus and hepatitis, and an LRV of greater than 6 may be obtained with larger sized virus such as the AIDS virus.

Surfactants

Surfactants that find use in the present invention may be non-ionic, anionic or cationic. Suitable non-ionic surfactants finding use in the present invention include, for example, polyoxyethylene sorbitan fatty esters such as polysorbates 20, 40, 60, 65, 80, etc. (Tween®), polyoxyethylene tert-octylphenols such as Triton® X-100, Triton® X-220, Triton® X-405, and Triton® X-460, polyoxyethylene nonylphenol (Igepal®), polyoxyethylene lauryl ethers (Brij® 35, laurylmacrogol), polyoxyethylene monohexyldecyl ether (Cetomacrogol), polyoxypropylene-polyoxyethylene ethers (including polyoxamers F 38, 68, 127, 108, L62, 184, 188, Poloxamer 124, 188, 237, 338, 407, etc.), Pluronic® polyols, polyoxyl 40 or 50 stearate (Myrj®), polyoxyl ester laurate, polyoxyl 35, polyoxyl 40, polyoxyl 10 oleyl ether, polyoxyl 20 cetostearyl ether, PEG 4-8 laurate, PEG 4-8 stearate, hydrogenated castor oil, polyoxyethylene hydrogenated castor oil (Emulphor®) 10, 50 and 60, glycerol monostearate, octylglucosides, sorbitan esters (Span®), sorbitan monolaurate, monopalmitate, mono-oleate, monostearate, sesquioleate, trioleate, sucrose fatty acid esters, octylglucosides, glyceryl esters, and the like. Anionic surfactants that find use in the present invention include, for example, sodium lauryl sulfate, sodium dodecyl sulfate, sodium fatty sulfosuccinate (Aerosol®), dioctyle sodium sulfosuccinate (Aerosol OT®), dihexyl sulfosuccinate (Aerosol MA®), sodium desoxycholate, sodium cholate, sodium glycocholate, sodium caprylate, sodium hexylsulphonate, and the like. Cationic surfactants that find use in the present invention include, for example, benzalkonium chloride, benzethonium chloride, cetylpyridinium chloride, cetyl trimethyl ammonium bromide, and the like. In some embodiments, ultrafiltration membrane fouling is reduced by adding polysorbate 20 directly to an aqueous solution containing virus particles and at least one protein prior to filtration. In some embodiments, ultrafiltration membrane fouling is reduced by adding Triton® X-100 directly to an aqueous solution containing virus particles and at least one protein prior to filtration.

Non-Surfactant, Non-Ionic Agents Useful in the Present Invention

Non-surfactant, non-ionic agents that find use in the present invention include, for example, polyethylene glycols (PEGs), preferably polyethylene glycols having molecular weights from about 400 to about 6000 g/mol, cellulose derivatives (such as, for example, methylcellulose, carboxymethylcellulose, hydroxyethylcellulose, and hydroxypropyl methylcellulose), arginine (including L-arginine, arginine-HCl, and the like), flavanone glycosides, naringin, rutin (quercetin rutinoside) and dextrans, preferably dextrans having molecular weights from about 2,000 to 20,000 Da, and the like. In some embodiments, the non-surfactant, non-ionic agent is not arginine.

In some embodiments of the invention, more than one non-surfactant, non-ionic agent is added to the aqueous solution prior to ultrafiltration to reduce fouling of the ultrafiltration membrane. In other embodiments, any combinations of surfactant(s) and non-surfactant, non-ionic agent(s) may be employed.

In some embodiments of the invention, more than one surfactant is added to the aqueous solution prior to ultrafiltration to reduce fouling of the ultrafiltration membrane. In some embodiments, more than one non-ionic surfactant is added to the aqueous solution. In other embodiments, more than one anionic surfactant is added to the aqueous solution. In other embodiments, more than one cationic surfactant is added to the aqueous solution. In other embodiments, any combinations of surfactant selected from non-ionic surfactants, anionic surfactants and cationic surfactants; for example, an non-ionic surfactant and an anionic surfactant, a non-ionic surfactant and a cationic surfactant, or an anionic surfactant and a cationic surfactant.

Feedstock

In some aspects, the invention provides methods of reducing fouling of ultrafiltration membranes used for the removal of viral particles from a feedstock produced during the manufacture of biological drugs by adding a surfactant or a non-surfactant, non-ionic agent to the feedstock prior to ultrafiltration. In some embodiments, the invention provides methods of increasing throughput of ultrafiltration membranes used for the removal of viral particles from a feedstock produced during the manufacture of biological drugs by adding a surfactant or a non-surfactant, non-ionic agent to the feedstock prior to ultrafiltration. In some embodiments, the invention provides methods of increasing the half-life of an ultrafiltration membrane used for the removal of viral particles from a feedstock produced during the manufacture of biological drugs by adding a surfactant or a non-surfactant, non-ionic agent to the feedstock prior to ultrafiltration. In some embodiments, the biological drug is a polypeptide or protein. In some embodiments the biological drug is an immunoglobulin; for example, an immunoadhesin or an antibody.

Feedstocks contemplated by the invention may be an aqueous solution comprising at least one protein. The feedstock is passed through an ultrafiltration membrane to remove virus particles that may be in the feedstock. The feedstock may be generated from any source. For example, the feedstock may be generated from a eukaryotic cell culture system used recombinantly to produce a protein of interest. In some embodiments of the invention, the eukaryotic cell culture is a mammalian cell culture; for example, a hamster cell culture, a human cell culture, a mouse cell culture and the like. In some embodiments of the invention, the feedstock is generated from an in vivo source.

In some embodiments of the invention, the feedstock comprising a protein of interest has been subject to separation processes prior to an ultrafiltration step. For example, the feedstock may be subject to chromatographic separation processes, centrifugation processes, gel filtration processes and/or precipitation processes. In some embodiments of the invention, the feedstock comprises a substantially purified protein.

The aqueous solution comprising viral particles and at least one protein may include any one of the following: buffers, salts, chelators, anti-oxidants, protease inhibitors, preservatives and the like appropriate for the protein of interest. The pH of the aqueous solution may be appropriate for the protein of interest. In some embodiments the pH of the aqueous solution ranges from about 3.4 to about 9.0, preferably from about 5.0 to 8.0, more preferably from about 6.0 to 8.0. The temperature of the feed stream may be appropriate for the protein of interest. In some embodiments the temperature of the aqueous solution ranges from about 2° C. to about 30° C., preferably from about 10° C. to 25° C. The concentration of the protein in the aqueous solution may range from about 1 g/mL to about 200 g/L, preferably from about 1 g/mL to about 50 g/L. One skilled in the art can determine the appropriate concentration for a particular protein.

The feedstock will contain at least one type of virus particle prior to ultrafiltration. In certain embodiments, the virus particle may be a parvovirus, a circovirus, or an endogeneous retrovirus.

The feedstock will contain at least one protein, which in one embodiment is an antibody. The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the $\alpha$ and $\gamma$ chains and four CH domains for $\mu$ and $\epsilon$ isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated $\alpha$, $\delta$, $\epsilon$, $\gamma$, and $\mu$, respectively. The $\gamma$ and $\alpha$ classes are further divided into subclasses on the basis of relatively minor differences in CH sequence and function, e.g., humans express the following subclasses: IgG1, IgG2, IgG3, IgG4, IgA1, and IgA2.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Antibody Engineering, 2nd edition (C. Borrebaeck, ed., Oxford University Press, 1995.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Prefilter

In some aspects the invention provides methods of reducing fouling of ultrafiltration membranes in processes where an aqueous solution comprising viral particles and at least one protein are subject to a prefilter step prior to ultrafiltration. An example of a system where a feedstock is subject to a prefilter step prior to ultrafiltration is provided by U.S. Pat. No. 7,118,675. The present invention provides methods of further reduction in the fouling of ultrafiltration membranes in processes that include a prefilter by adding a surfactant or a non-surfactant, non-ionic agent to the aqueous solution comprising viral particles and at least one protein prior to ultrafiltration. In some embodiments, the surfactant or a non-surfactant, non-ionic agent is added prior to a prefilter step. In other embodiments, the surfactant or a non-surfactant, non-ionic agent is added to the aqueous solution after a prefilter step but before ultrafiltration. In some embodiments of the invention, more than one prefilter or prefiltration step is used. In some embodiments of the invention, the surfactant or a non-surfactant, non-ionic agent is added to the aqueous solution before a first prefilter step, before a second prefilter step or after one or more prefilters but prior to ultrafiltration.

In some embodiments of the invention, the prefilter comprises one or more layers of adsorptive depth filters. In some embodiments of the invention, the prefilter comprises one or more layers of charged or surface modified microporous membranes. Representative suitable prefilters include those formed from fibrous media formed of cellulosic fibers, synthetic fibers or blends thereof, such as MILLISTAK®+ pads; microporous membranes which are either charged or have a surface chemistry (such as hydrophilicity or hydrophobicity or a positive or negative charge as are taught by U.S. Pat. Nos. 5,629,084 and 4,618,533) made from a material selected from the group consisting of regenerated cellulose, polyethersulfone, polyarylsulphone, polysulfone, polyimide, polyamide or polyvinylidenedifluoride (PVDF), such as charged Durapore® membrane, hydrophobic Durapore® membrane, hydrophobic Aervent® membrane and Intercept™ Q quaternary charged membrane; and chromatography media including size exclusion media, ion exchange media, hydrophobic media and the like such as Cellufine® hydrophobic media, PEIL-1000 media, Cellufine® ion exchange, and Matrex® chromatography media. In some embodiments the prefilter is a Mustang® S filter. In some embodiments the prefilter is an AIHC filter. In some embodiments, the prefilter is a XOHC filter. Other prefilters that find use in the present invention include, for example, Millipore Viresolve® Pro+, Viresolve® Shield, Intercept Q, ChromaSorb™, Pall Mustang® S, Mustang® E, Mustang® Q, Sartorius Stedim Sartobind® S, Sartobind® C, Sartobind® Q, Sartobind® D, Sartobind® STIC, Sartobind® HIC, Natrix Q, S, C membrane adsorbers, Pall STAX™, SUPRAcap™, SUPRAdisc 1 and SUPRAdisc 2 depth filters EKSP, EK1, EK, KS 50, KS 80, K100, K150, K200, K250, K300, K700, K900, K100 IR, K250 IR, K800 IR, K900 IR, T950, T1000, T2100, T2600, T3500, T5500, Sartorius Stedim Sartoclear® P depth filter cartridges and pads C4, CH8, F4H, F7H, S5, S9, Begerow BECODISC, Begerow BECOPAD, Begerow BECODISC BS, CUNO depth filters ZETA Plus™ EXT ZA, EXT SP, ZA, LP, LA, AP, SP, and VR.

Methods to Reduce Membrane Fouling

The invention provides methods of reducing fouling of an ultrafiltration membrane in a process wherein virus particles are removed from an aqueous solution comprising said virus particles and at least one protein, comprising the steps of a) adding a surfactant or a non-surfactant, non-ionic agent to said aqueous solution, and b) filtering said aqueous solution comprising said surfactant or a non-surfactant, non-ionic agent through one or more ultrafiltration membranes. The inventors have discovered that adding a surfactant directly to the aqueous solution reduces fouling of the ultrafiltration membrane.

In the present invention, addition of a surfactant or a non-surfactant, non-ionic agent to the protein-containing feedstream prior to ultrafiltration will enhance the filtration throughput efficiency of the ultrafiltration membrane by a quantatatively measurable amount. As described above, "enhancing the filtration throughput efficiency", and the like, when used in reference to an ultrafiltration membrane refers to the beneficial effect of increased volume throughput through an ultrafiltration membrane caused by addition of a surfactant or certain non-surfactant, non-ionic agent(s) to a protein-containing aqueous solution prior to filtration of that aqueous solution through the ultrafiltration membrane. To quantatively determine the degree in enhancement of ultrafiltration throughput efficiency as a result of the addition of a surfactant or a non-surfactant, non-ionic agent to the feedstream prior to ultrafiltration, quantitative comparisons can be made by filtering the aqueous solution (both with and without the addition of a surfactant or non-surfactant, non-ionic agent) through an ultrafiltration membrane at a constant transmembrane pressure, and then measuring the throughput volume over time. In more specific regard and for example, enhancing the filtration throughput efficiency of an ultrafiltration membrane by at least 10% means that the volume throughput of the membrane per unit time and at a constant pressure is at least 10% higher in the presence of a surfactant or non-surfactant, non-ionic agent than it is over the same unit time and same constant pressure in the absence of a surfactant or non-surfactant, non-ionic agent.

Although the surfactant or non-surfactant, non-ionic agent can be added to the aqueous solution in any useful amount to reduce fouling of ultrafiltration membranes, in some embodiments the surfactant or non-surfactant, non-ionic agent is added to the aqueous solution at a concentration ranging from about 1 PPM to about 10,000 PPM. In some embodiments of the invention, the concentration of the surfactant or non-surfactant, non-ionic agent ranges from about 10 PPM to about 1000 PPM. In some embodiments of the invention, the concentration of the surfactant or non-surfactant, non-ionic agent ranges from about 100 PPM to about 1000 PPM. In some embodiments of the invention, the concentration of the surfactant or non-surfactant, non-ionic agent ranges from about 10 PPM to about 200 PPM. In some embodiments of the invention, the concentration of the surfactant or non-surfactant, non-ionic agent ranges from about 10 PPM to about 100 PPM. In some embodiments of the invention, the concentration of the surfactant or non-surfactant, non-ionic agent ranges from about 20 PPM to about 200 PPM. In some embodiments of the invention, the concentration of the surfactant or non-surfactant, non-ionic agent ranges from about 20 PPM to about 100 PPM. In some embodiments the surfactant or non-surfactant, non-ionic agent is added to the aqueous solution at a concentration of less than about any of 1 PPM, 5 PPM, 10 PPM, 20 PPM, 30 PPM, 40 PPM, 50 PPM, 60 PPM, 70 PPM, 80 PPM, 90 PPM, 100 PPM, 110 PPM, 120 PPM, 130 PPM, 140 PPM, 150 PPM, 160 PPM, 170 PPM, 180 PPM, 190 PPM, 200 PPM, 225 PPM, 250 PPM, 275 PPM, 300 PPM, 350 PPM, 400 PPM, 450 PPM, 500 PPM, 600 PPM, 700 PPM, 800 PPM, 900 PPM, 1000 PPM, 1250 PPM, 1500 PPM, 1750 PPM, 2000 PPM, 3000 PPM, 4000 PPM, 5000 PPM, 6000 PPM, 7000 PPM, 8000 PPM, 9000 PPM, 10,000 PPM, or greater than about 10,000 PPM.

In some embodiments of the invention, one or more surfactants or non-surfactant, non-ionic agents are added to a feed stream of an aqueous solution comprising viral particles and at least one protein prior to ultrafiltration. In some embodiments, the one or more surfactants or non-surfactant, non-ionic agents are added to a bulk aqueous solution of viral particles and at least one protein prior to ultrafiltration.

In some aspects, the invention provides methods of reducing fouling of an ultrafiltration membrane in a process where virus particles are removed from an aqueous solution comprising virus particles and at least one protein where the aqueous solution is passed through a prefilter prior to ultrafiltration. In some embodiments of the invention, the method comprises the steps of a) filtering the aqueous solution through prefilter; b) adding a surfactant or non-surfactant, non-ionic agent to the aqueous solution; and c) filtering the aqueous solution comprising the surfactant or non-surfactant, non-ionic agent through one or more ultrafiltration membranes, where the presence of the surfactant in the aqueous solution reduces fouling of the ultrafiltration membrane. In other embodiments of the invention, the method comprises the steps of a) adding a surfactant or non-surfactant, non-ionic agent to the aqueous solution; b) filtering the aqueous solution through a prefilter; and c) filtering the aqueous solution comprising the surfactant or non-surfactant, non-ionic agent through one or more ultrafiltration membranes, wherein the presence of the surfactant or non-surfactant, non-ionic agent in the aqueous solution reduces fouling of the ultrafiltration membrane. In some embodiments, the prefilter is one or more layers of adsorptive depth filters or one or more layers of charged or surface modified microporous membranes. The degree of fouling of an ultrafiltration membrane may be determined by measuring the mass throughput of the membrane.

In one aspect, quantitative comparisons can be made by filtering the protein-containing aqueous solution (both with and without the addition of a surfactant or non-surfactant, non-ionic agent) through an ultrafiltration membrane at a constant transmembrane pressure, and then measuring the throughput volume over time through the membrane. Generally, such quantitative comparisons can be made by maintaining a constant transmembrane pressure for a predetermined period of time, wherein such constant transmembrane pressure is usually in the range between about 5 psi to about 45 psi, preferably is 40 psi. Also, for such quantititive comparisons, virtually any predetermined period of time may be employed and the time required for detecting measurable differences in throughput volume will differ based upon certain aqueous solution variables such as protein concentration, level of foulants in the aqueous solution, etc., however, it is preferred that the time period be in the range between about 5 minutes and 360 minutes, preferably in the range between about 10 minutes and 240 minutes, more preferably 60 minutes.

In more specific regard and for example, enhancing the filtration throughput efficiency of an ultrafiltration membrane by at least 10% means that the volume throughput of the membrane over a predetermined until of time (as described above, preferably a time period anywhere in the range from about 5 minutes to about 360 minutes) and at a constant transmembrane pressure (preferably 40 psi) is at least 10% higher in the presence of a surfactant or non-surfactant, non-ionic agent (and or implementation of at least one prefiltration step) than it is over the same unit time and same constant pressure in the absence of the surfactant or non-surfactant, non-ionic agent.

Membrane fouling may also be determined by measuring changes in flux. In some embodiments flux is measured as LMH ($L/m^2/hr$) which represents the liters of aqueous solution that pass through a membrane with a specific area in an hour. As a membrane becomes fouled the flux decreases.

Membrane fouling may also be determined by measuring throughput of a protein in an aqueous solution at a predetermined endpoint transmembrane pressure. As the membrane becomes fouled, the transmembrane pressure increases. In some cases, the pressure will increase beyond the capacity of the membrane and the filtration will need to be stopped. One skilled in the art would recognize an appropriate endpoint transmembrane pressure for a given ultrafiltration membrane. An indication of membrane fouling, therefore, would be suggested by a low throughput at a predetermined transmembrane endpoint; for example, 40 psi for a VPro ultrafiltration membrane. A membrane with little or no fouling would result in a high throughput; for example, greater than 6000 $g/m^2$ at less than or equal to 40 psi. In some cases, where little membrane fouling occurs, the endpoint pressure may not be reached. In these cases, the extent of membrane fouling may be indicated by the observed transmembrane pressure at the greatest protein throughput. In some embodiments of the invention, filter performance can be assessed by plotting transmembrane pressure (e.g. in pounds per square inch) against mass throughput (e.g. $g/m^2$, where $m^2$ is the cross-sectional area of the membrane). In some embodiments of the invention, filter performance can be assessed by plotting the differential transmembrane pressure (e.g. in pounds per square inch differential) against mass throughput (e.g. $g/m^2$).

The invention provides methods to measure the retention of virus by ultrafiltration membranes. Methods to measure virus particles are known in the art and include, but are not limited to immunoassays, viral nucleic acid hybridization, PCR, viral titer assays and the like. The log retention value (LRV) can be measured by comparing the amount of virus in the aqueous solution feedstock before ultrafiltration with the amount of virus in the ultrafiltration permeate. In some embodiments, the invention provides methods to reduce fouling of an ultrafiltration membrane by adding a surfactant or a non-surfactant, non-ionic agent to an aqueous solution of virus and at least one protein where at least three logs of the virus in the aqueous solution are retained by the ultrafiltration membrane. In some embodiments of the invention a surfactant or a non-surfactant, non-ionic agent is added to an aqueous solution comprising virus and at least one protein wherein fouling of the ultrafiltration membrane is reduced and wherein viral retention by the ultrafiltration membrane is essentially unchanged.

Methods to Dissociate Protein Aggregates or Reduce the Formation of Protein Aggregates In some aspects, the invention provides methods to dissociate protein aggregates and/or to reduce protein aggregation in an ultrafiltration feed stream comprising an aqueous solution comprising at least one protein. The method comprises adding a surfactant or a non-surfactant, non-ionic agent to the aqueous solution. In some embodiments, dissociation of protein aggregation or reduction in the formation of protein aggregates may reduce the fouling of the ultrafiltration membrane. An aggregate refers to any multimers of a polypeptide or a polypeptide fragment (e.g. a dimer, a trimer, a tetramer, or a multimer greater than a tetramer).

In some embodiments of the invention, the addition of a surfactant or a non-surfactant, non-ionic agent is capable of reducing protein aggregation in a protein-containing aqueous solution by at least 10%, at least 20%, at least 30%, at least 40%, at least 50%, at least 60%, at least 70%, at least 80%, at least 90%, or at least 100%, when compared to the amount of protein aggregation present in the same aqueous solution lacking the surfactant or non-surfactant, non-ionic agent. Quantitative determination and comparison of the amount of protein aggregation in aqueous solutions lacking versus containing a surfactant or non-surfactant, non-ionic agent can be made using well known techniques in the art.

In some embodiments of the invention, the addition of a surfactant or a non-surfactant, non-ionic agent is capable of reducing the average number of protein aggregates in an aqueous solution by at least about any of 10%, 20%, 30%, 40%, 50%, 60%, 70%, 80%, 90%, or 100%, when compared to the average number of protein aggregates present in the same aqueous solution lacking the surfactant or non-surfactant, non-ionic agent. Quantitative determination and comparison of the average number of protein aggregates in aqueous solutions lacking versus containing a surfactant or non-surfactant, non-ionic agent can be made using well known techniques in the art.

In some embodiments of the invention, the addition of a surfactant or a non-surfactant, non-ionic agent is capable of reducing the average protein aggregate size in an aqueous solution by about any of 10%, 20%, 30%, 40%, 50%, 60%, 70%, 80%, 90%, or 100%, when compared to the average protein aggregate size present in the same aqueous solution lacking the surfactant or non-surfactant, non-ionic agent. Quantitative determination and comparison of the average protein aggregate size in aqueous solutions lacking versus containing a surfactant or a non-surfactant, non-ionic agent can be made using well known techniques in the art. In some embodiments, the average protein aggregate size is reduced by at least about any of the above-referenced amounts.

Although the surfactant or non-surfactant, non-ionic agent can be added to the aqueous solution in any useful amount to dissociate existing protein aggregates and/or to prevent the formation of new protein aggregates, in some embodiments the surfactant or non-surfactant, non-ionic agent is added to the aqueous solution at a concentration ranging from about 1 PPM to about 10,000 PPM. In some embodiments of the invention, the concentration of the surfactant or non-surfactant, non-ionic agent ranges from about 10 PPM to about 1000 PPM. In some embodiments of the invention, the concentration of the surfactant or non-surfactant, non-ionic agent ranges from about 100 PPM to about 1000 PPM. In some embodiments of the invention, the concentration of the surfactant or non-surfactant, non-ionic agent ranges from about 10 PPM to about 200 PPM. In some embodiments of the invention, the concentration of the surfactant or non-surfactant, non-ionic agent ranges from about 10 PPM to about 100 PPM. In some embodiments of the invention, the concentration of the surfactant or non-surfactant, non-ionic agent ranges from about 20 PPM to about 200 PPM. In some embodiments of the invention, the concentration of the surfactant or non-surfactant, non-ionic agent ranges from about 20 PPM to about 100 PPM. In some embodiments the surfactant or non-surfactant, non-ionic agent is added to the aqueous solution at a concentration of less than 1 PPM, 5 PPM, 10 PPM, 20 PPM, 30 PPM, 40 PPM, 50 PPM, 60 PPM, 70 PPM, 80 PPM, 90 PPM, 100 PPM, 110 PPM, 120 PPM, 130 PPM, 140 PPM, 150 PPM, 160 PPM, 170 PPM, 180 PPM, 190 PPM, 200 PPM, 225 PPM, 250 PPM, 275 PPM, 300 PPM, 350 PPM, 400 PPM, 450 PPM, 500 PPM, 600 PPM, 700 PPM, 800 PPM, 900 PPM, 1000 PPM, 1250 PPM, 1500 PPM, 1750 PPM, 2000 PPM, 3000 PPM, 4000 PPM, 5000 PPM, 6000 PPM, 7000 PPM, 8000 PPM, 9000 PPM, 10,000 PPM, or greater than 10,000 PPM.

In some embodiments of the invention, surfactants that find use for dissociating existing protein aggregates and/or preventing the formation of protein aggregates in aqueous protein-containing solutions may be non-ionic, anionic or cationic. Suitable non-ionic surfactants finding use in the present invention include, for example, polyoxyethylene sorbitan fatty esters such as polysorbates 20, 40, 60, 65, 80, etc. (Tween®), polyoxyethylene tert-octylphenols such as Triton® X-100, Triton® X-220, Triton® X-405, and Triton® X-460, polyoxyethylene nonylphenol (Igepal®), polyoxyethylene lauryl ethers (Brij® 35, Laurylmacrogol), polyoxyethylene monohexyldecyl ether (Cetomacrogol), polyoxypropylene-polyoxyethylene ethers (including poly-oxamers F 38, 68, 127, 108, L62, 184, 188, Poloxamer 124, 188, 237, 338, 407, etc.), Pluronic® polyols, polyoxyl 40 or 50 stearate (Myrj®), polyoxyl ester laurate, polyoxyl 35, polyoxyl 40, polyoxyl 10 oleyl ether, polyoxyl 20 cetostearyl ether, PEG 4-8 laurate, PEG 4-8 stearate, hydrogenated castor oil, polyoxyethylene hydrogenated castor oil (Emulphor®) 10, 50 and 60, glycerol monostearate, octylglucosides, sorbitan esters (Span®), sorbitan monolaurate, monopalmitate, mono-oleate, monostearate, sesquioleate, trioleate, sucrose fatty acid esters, octylglucosides, glyceryl esters, and the like. Anionic surfactants that find use in the present invention include, for example, sodium lauryl sulfate, sodium dodecyl sulfate, sodium fatty sulfosuccinate (Aerosol®), dioctyle sodium sulfosuccinate (Aerosol OT®), dihexyl sulfosuccinate (Aerosol MA®), sodium desoxycholate, sodium cholate, sodium glycocholate, sodium caprylate, sodium hexylsulphonate, and the like. Cationic surfactants that find use in the present invention include, for example, benzalkonium chloride, benzethonium chloride, cetylpyridinium chloride, cetyl trimethyl ammonium bromide, and the like.

In some embodiments of the invention, more than one surfactant is added to the aqueous solution to dissociate preexisting protein aggregates and/or to prevent the formation of protein aggregates in a protein-containing solution. In some embodiments, more than one non-ionic surfactant is added to the aqueous solution. In other embodiments, more than one anionic surfactant is added to the aqueous solution. In other embodiments, more than one cationic surfactant is added to the aqueous solution. In other embodiments, any combinations of surfactant selected from non-ionic surfactants, anionic surfactants and cationic surfactants; for example, a non-ionic surfactant and an anionic surfactant, a non-ionic surfactant and a cationic surfactant, or an anionic surfactant and a cationic surfactant.

Non-surfactant, non-ionic agents that find use for dissociating preexisting protein aggregates and/or preventing the formation of new protein aggregates in aqueous protein-containing solutions include, for example, polyethylene glycols (PEGs), preferably polyethylene glycols having molecular weights from about 400 to about 6000 g/mol, methylcellulose, carboxymethylcellulose, hydroxyethylcellulose, hydroxypropyl methylcellulose, arginine (including L-arginine, arginine-HCl, and the like), flavanone glycosides, naringin, rutin (quercetin rutinoside) and dextrans, preferably dextrans having molecular weights from about 2,000 to 20,000 Da, and the like.

In some embodiments of the invention, more than one non-surfactant, non-ionic agent is added to the aqueous solution. In other embodiments, any combinations of surfactant(s) and non-surfactant, non-ionic agent(s) may be employed.

In some embodiments, the methods of reducing protein aggregation or reducing the formation of protein aggregates further comprise the step of filtering the aqueous solution comprising the protein and the surfactant or non-surfactant, non-ionic agent through an ultrafiltration membrane. In some embodiments, the ultrafiltration membrane is a parvovirus retentive membrane or a membrane capable of removing parvovirus. In some embodiments, the filtration is by normal flow filtration. In other embodiments, the filtration is by tangential flow filtration. In some embodiments of the invention, remaining aggregates are removed from the aqueous solution by ultrafiltration.

In some embodiments, the methods of reducing protein aggregation or reducing the formation of protein aggregates further comprise a prefilter step and an ultrafiltration step. In some embodiments, the method comprises the steps of a) filtering the aqueous solution through prefilter; b) adding a surfactant or a non-surfactant, non-ionic agent to the aqueous solution to dissociate protein aggregates or prevent the formation of protein aggregates; and c) filtering the aqueous solution comprising the surfactant or non-surfactant, non-ionic agent through one or more ultrafiltration membranes. In other embodiments of the invention, the method comprises the steps of a) adding a surfactant or non-surfactant, non-ionic agent to the aqueous solution to dissociate protein aggregates or prevent the formation of protein aggregates; b) filtering the aqueous solution through a prefilter; and c) filtering the aqueous solution comprising the surfactant or non-surfactant, non-ionic agent through one or more ultrafiltration membranes. In some embodiments, the prefilter is one or more layers of adsorptive depth filters or one or more layers of charged or surface modified microporous membranes.

Methods to measure protein aggregation are known in the art. For example, a liquid particle counting system that uses light obscuration analysis can be used to determine the number of particles of a specific size range. In some embodiments of the invention, reduction of protein aggregation can be determined by comparing the total number of particles in an aqueous solution of proteins in the presence of a surfactant or non-surfactant, non-ionic agent with the total number of particles in an aqueous solution of proteins in the absence of a surfactant or non-surfactant, non-ionic agent. In some embodiments of the invention, reduction of protein aggregation can be determined by comparing the average size of particles in an aqueous solution of proteins in the presence of a surfactant or non-surfactant, non-ionic agent with the average size of particles in an aqueous solution of proteins in the absence of a surfactant or non-surfactant, non-ionic agent.

EXEMPLARY EMBODIMENTS

In one aspect, the invention provides methods of reducing fouling of an ultrafiltration membrane in a process wherein virus particles are removed from an aqueous solution comprising said virus particles and at least one protein, the method comprising the steps of a) adding to said aqueous solution a surfactant or a non-surfactant, non-ionic agent selected from the group consisting of a polyethylene glycol, a cellulose derivative, arginine, and a dextran, and b) filtering said aqueous solution comprising said surfactant or said non-surfactant, non-ionic agent through said ultrafiltration membranes, wherein the presence of said surfactant or said non-surfactant, non-ionic agent in said aqueous solution reduces fouling of said ultrafiltration membrane.

In one embodiment of the above method, the surfactant is a non-ionic surfactant. In one embodiment of any of the above methods, the non-ionic surfactant is selected from the group consisting of polysorbate 20, Triton® X-100, Triton® X-405, lauromacrogol, and polysorbate 80. In one embodiment of any of the above methods the surfactant is polysorbate 20.

In one embodiment of any of the above methods, the surfactant or non-surfactant, non-ionic agent is added to said aqueous solution at a concentration of 1-10,000 PPM. In one embodiment of any of the above methods, the surfactant or non-surfactant, non-ionic agent is added to said aqueous solution at a concentration of 10-200 PPM.

In one embodiment of any of the above methods, the ultrafiltration membrane is a parvovirus retentive membrane. In one embodiment of any of the above methods, the ultrafiltration membrane has a pore size of less than about 100 nm or less. In one embodiment of any of the above methods, the ultrafiltration membrane has a pore size of about 20 nm or less.

In one embodiment of any of the above methods, the step of filtering said aqueous solution is by normal flow filtration.

In one embodiment of any of the above methods, the protein is an antibody. In one embodiment of any of the above methods, the antibody is a monoclonal or humanized antibody.

In one embodiment of the above method, the addition of said surfactant or said non-surfactant, non-ionic agent to said aqueous solution enhances the filtration throughput efficiency of said ultrafiltration membrane by at least 10%. In one embodiment of any of the above methods, the addition of said surfactant or said non-surfactant, non-ionic agent to said aqueous solution enhances the filtration throughput efficiency of said ultrafiltration membrane by at least 50%.

In one embodiment of any of the above methods, the virus particles are parvovirus particles.

In one embodiment of any of the above methods, the method further comprises the step of filtering said aqueous solution through one or more layers of adsorptive depth filters or one or more layers of charged or surface modified microporous membranes, prior to the filtration of said aqueous solution through said ultrafiltration membrane.

In another aspect, the invention provides methods of enhancing the filtration throughput efficiency of an ultrafiltration membrane in a process wherein virus particles are removed from an aqueous solution comprising said virus particles and at least one protein, the method comprising adding a surfactant or a non-surfactant, non-ionic agent selected from the group consisting of a polyethylene glycol, a cellulose derivative, arginine, and a dextran to said aqueous solution before filtering said aqueous solution through said ultrafiltration membranes, wherein the presence of said surfactant or said non-surfactant, non-ionic agent in said aqueous solution enhances the filtration throughput efficiency of said ultrafiltration membrane as compared to in the absence of said surfactant or non-surfactant, non-ionic agent.

In one embodiment of the above method wherein said surfactant is a non-ionic surfactant. In one embodiment of any of the above methods, the non-ionic surfactant is selected from the group consisting of polysorbate 20, Triton® X-100, Triton® X-405, lauromacrogol, and polysorbate 80. In one embodiment of any of the above methods, the surfactant is polysorbate 20.

In one embodiment of any of the above methods, the surfactant or non-surfactant, non-ionic agent is added to said aqueous solution at a concentration of 1-10,000 PPM. In one embodiment of any of the above methods, the surfactant or non-surfactant, non-ionic agent is added to said aqueous solution at a concentration of 10-200 PPM.

In one embodiment of any of the above methods, the ultrafiltration membrane is a parvovirus retentive membrane. In one embodiment of any of the above methods, the ultrafiltration membrane has a pore size of less than about 100 nm or less. In one embodiment of any of the above methods, the ultrafiltration membrane has a pore size of about 20 nm or less.

In one embodiment of any of the above methods, the step of filtering said aqueous solution is by normal flow filtration.

In one embodiment of any of the above methods, the protein is an antibody. In one embodiment of any of the above methods, the antibody is a monoclonal or humanized antibody.

In one embodiment of any of the above methods, the addition of said surfactant or said non-surfactant, non-ionic agent to said aqueous solution enhances the filtration throughput efficiency of said ultrafiltration membrane by at least 10%. In one embodiment of any of the above methods, the addition of said surfactant or said non-surfactant, non-ionic agent to said aqueous solution enhances the filtration throughput efficiency of said ultrafiltration membrane by at least 50%.

In one embodiment of any of the above methods, the virus particles are parvovirus particles.

In one embodiment of any of the above methods, the method further comprises the step of filtering said aqueous solution through one or more layers of adsorptive depth filters or one or more layers of charged or surface modified microporous membranes, prior to the filtration of said aqueous solution through said ultrafiltration membrane.

In another aspect, the invention provides methods to dissociate polypeptide aggregates or reduce the formation of polypeptide aggregates in an ultrafiltration feed stream comprising an aqueous solution comprising at least one protein, the method comprising adding a surfactant or a non-surfactant, non-ionic agent selected from the group consisting of a polyethylene glycol, a cellulose derivative, arginine and a dextran to said aqueous solution.

In one embodiment of the above method, the surfactant is a non-ionic surfactant. In one embodiment of any of the above methods, the non-ionic surfactant is selected from the group consisting of polysorbate 20, Triton® X-100, Triton® X-405, lauromacrogol, and polysorbate 80. In one embodiment of any of the above methods, the surfactant is polysorbate 20.

In one embodiment of any of the above methods, the surfactant or non-surfactant, non-ionic agent is added to said aqueous solution at a concentration of 1-10,000 PPM. In one embodiment of any of the above methods, the surfactant or non-surfactant, non-ionic agent is added to said aqueous solution at a concentration of 10-200 PPM.

In one embodiment of any of the above methods, the method further comprises the step of filtering said aqueous solution comprising said surfactant or non-surfactant, non-ionic agent through an ultrafiltration membrane. In one embodiment of any of the above methods, the ultrafiltration membrane is a parvovirus retentive membrane. In one embodiment of any of the above methods, the ultrafiltration membrane has a pore size of less than about 100 nm or less. In one embodiment of any of the above methods, the ultrafiltration membrane has a pore size of about 20 nm or less. In one embodiment of any of the above methods, the step of filtering said aqueous solution is by normal flow filtration.

In one embodiment of any of the above methods, the protein is an antibody. In one embodiment of any of the above methods, the antibody is a monoclonal or humanized antibody.

In one embodiment of any of the above methods, the addition of said surfactant or said non-surfactant, non-ionic agent to said aqueous solution enhances the filtration throughput efficiency of said ultrafiltration membrane by at least 10%. In one embodiment of any of the above methods, the addition of said surfactant or said non-surfactant, non-ionic agent to said aqueous solution enhances the filtration throughput efficiency of said ultrafiltration membrane by at least 50%.

In one embodiment of any of the above methods, the method further comprises the step of filtering said aqueous solution through one or more layers of adsorptive depth filters or one or more layers of charged or surface modified microporous membranes, prior to the filtration of said aqueous solution through said ultrafiltration membrane.

In another aspect, the invention provides methods of reducing fouling of an ultrafiltration membrane in a process wherein virus particles are removed from an aqueous solution comprising said virus particles and at least one protein, the method comprising the steps of a) filtering said aqueous solution through a device selected from the group consisting of one or more layers of adsorptive depth filters and one or more layers of charged or surface modified microporous membranes; b) adding a surfactant or non-surfactant, non-ionic agent selected from the group consisting of a polyethylene glycol, a cellulose derivative, arginine and a dextran to said aqueous solution; and c) filtering said aqueous solution comprising said surfactant or said non-surfactant, non-ionic agent through said ultrafiltration membranes, wherein the presence of said surfactant or said non-surfactant, non-ionic agent in said aqueous solution reduces fouling of said ultrafiltration membrane.

In one embodiment of the above method, the surfactant is a non-ionic surfactant. In one embodiment of any of the above methods, the non-ionic surfactant is selected from the group consisting of polysorbate 20, Triton® X-100, Triton® X-405, lauromacrogol, and polysorbate 80. In one embodiment of any of the above methods, the surfactant is polysorbate 20.

In one embodiment of any of the above methods, the surfactant or non-surfactant, non-ionic agent is added to said aqueous solution at a concentration of 1-10,000 PPM. In one embodiment of any of the above methods, the surfactant or non-surfactant, non-ionic agent is added to said aqueous solution at a concentration of 10-200 PPM.

In one embodiment of any of the above methods, the ultrafiltration membrane is a parvovirus retentive membrane. In one embodiment of any of the above methods, the ultrafiltration membrane has a pore size of less than about 100 nm or less. In one embodiment of any of the above methods, the ultrafiltration membrane has a pore size of about 20 nm or less.

In one embodiment of any of the above methods, the step of filtering said aqueous solution is by normal flow filtration.

In one embodiment of any of the above methods, the protein is an antibody. In one embodiment of any of the above methods, the antibody is a monoclonal or humanized antibody.

In one embodiment of any of the above methods, the addition of said surfactant or said non-surfactant, non-ionic agent to said aqueous solution enhances the filtration throughput efficiency of said ultrafiltration membrane by at least 10%. In one embodiment of any of the above methods, the addition of said surfactant or said non-surfactant, non-ionic agent to said aqueous solution enhances the filtration throughput efficiency of said ultrafiltration membrane by at least 50%.

In one embodiment of any of the above methods, the virus particles are parvovirus particles.

In another aspect, the invention provides methods of reducing fouling of an ultrafiltration membrane in a process wherein virus particles are removed from an aqueous solution comprising said virus particles and at least one protein, the method comprising the steps of a) adding a surfactant or non-surfactant, non-ionic agent selected from the group consisting of a polyethylene glycol, a cellulose derivative, arginine and a dextran to said aqueous solution, b) filtering said aqueous solution through a device selected from the group consisting of one or more layers of adsorptive depth filters and one or more layers of charged or surface modified microporous membranes; and c) filtering said aqueous solution comprising said surfactant or said non-surfactant, non-ionic agent through said ultrafiltration membranes, wherein the presence of said surfactant or said non-surfactant, non-ionic agent in said aqueous solution reduces fouling of said ultrafiltration membrane.

In one embodiment of the above method, the surfactant is a non-ionic surfactant. In one embodiment of any of the above methods, the non-ionic surfactant is selected from the group consisting of polysorbate 20, Triton® X-100, Triton® X-405, lauromacrogol, and polysorbate 80. In one embodiment of any of the above methods, the surfactant is polysorbate 20.

In one embodiment of any of the above methods, the surfactant or non-surfactant, non-ionic agent is added to said aqueous solution at a concentration of 1-10,000 PPM. In one embodiment of any of the above methods, the surfactant or non-surfactant, non-ionic agent is added to said aqueous solution at a concentration of 10-200 PPM.

In one embodiment of any of the above methods, the ultrafiltration membrane is a parvovirus retentive membrane. In one embodiment of any of the above methods, the ultrafiltration membrane has a pore size of less than about 100 nm or less. In one embodiment of any of the above methods, the ultrafiltration membrane has a pore size of about 20 nm or less.

In one embodiment of any of the above methods, the step of filtering said aqueous solution is by normal flow filtration.

In one embodiment of any of the above methods, the protein is an antibody. In one embodiment of any of the above methods, the antibody is a monoclonal or humanized antibody.

In one embodiment of any of the above methods, the addition of said surfactant or said non-surfactant, non-ionic agent to said aqueous solution enhances the filtration throughput efficiency of said ultrafiltration membrane by at least 10%. In one embodiment of any of the above methods, the addition of said surfactant or said non-surfactant, non-ionic agent to said aqueous solution enhances the filtration throughput efficiency of said ultrafiltration membrane by at least 50%.

In one embodiment of any of the above methods, the virus particles are parvovirus particles.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1: The Effect of Polysorbate 20 on Ultrafiltration Membrane Performance In an effort to determine the effect that certain surfactant or non-surfactant, non-ionic agent additives might have on the efficiency of ultrafiltration of various antibody-containing aqueous solutions, the aqueous feed solutions shown in Table 1 below were prepared and employed in the following described experiments.

TABLE 1

| Antibody | pH | Buffer | Antibody Concentration |
|---|---|---|---|
| Anti-PDL1 antibody | 6.0 | 0.110M sodium acetate, 0.024M MES | 5.56 mg/mL |
| Anti-DR5 antibody | 6.0 | 65 mM Tris, 38 mM phosphoric acid | 11.82 mg/mL |
| Anti-VEGF antibody | 5.5 | 0.086M acetic acid, 0.10M Tris base, 0.019M citric acid | 5.05 mg/mL |
| Anti-HER2 antibody | 5.6 | 0.25M HEPES 0.030M sodium acetate | 15.96 mg/mL |
| Anti-MUC16 antibody | 5.5 | 0.2M sodium acetate | 7.02 mg/mL |

To measure the effect that an added surfactant has on the rate of fouling of an ultrafiltration membrane, the aqueous protein-containing feed solutions described in Table 1 (either with or without the addition of a surfactant agent) were filtered through a Viresolve® Pro ultrafiltration membrane (Millipore Corporation). Filtration of the various protein-containing solutions through the ultrafiltration membrane was conducted at a starting transmembrane pressure of about 10 psi and the transmembrane pressure (due to fouling of the ultrafiltration membrane) was allowed to build until a transmembrane pressure of about 50 psi was reached, at which time the ultrafiltration process was stopped. If fouling of the ultrafiltration membrane did not substantially occur, the ultrafiltration process was stopped prior to reaching a transmembrane pressure of about 50 psi. Antibody throughput (measured by $g/m^2$ membrane surface area) was then determined and graphed against transmembrane pressure. The endpoint pressure of the filtration was 40 psi unless noted.

The data obtained from experiments measuring the effect of various concentrations of polysorbate 20 on ultrafiltration membrane fouling with various different aqueous solutions comprising different antibody molecules are shown in FIGS. 1 to 4. As shown in FIGS. 1 to 4, adding as little as 20 PPM of polysorbate 20 to an aqueous antibody-containing solution has a beneficial and reproducible effect on preventing fouling of the ultrafiltration membrane during the ultrafiltration process. The beneficial anti-fouling effect of polysorbate 20 is demonstrated with aqueous solutions comprising very different antibodies and over a broad range of polysorbate 20 concentrations tested. These data clearly demonstrate that non-ionic surfactants such as polysorbate 20 are useful as additives that may be employed in protein-containing feed streams for reducing or preventing fouling of ultrafiltration membranes during the ultrafiltration process.

Example 2: The Effect of Triton® X-100 on Ultrafiltration Membrane Performance In a second set of experiments, the effect of adding Triton® X-100 on the rate of fouling of an ultrafiltration membrane was determined as described in Example 1 above. The data obtained from experiments measuring the effect of various concentrations of Triton® X-100 on ultrafiltration membrane fouling with various different aqueous solutions comprising different antibody molecules are shown in FIGS. 4 to 7. As shown in FIGS. 4 to 7, adding as little as 20 PPM of Triton® X-100 to an aqueous antibody-containing solution has a beneficial and reproducible effect on preventing fouling of the ultrafiltration membrane during the ultrafiltration process. The beneficial anti-fouling effect of Triton® X-100 is demonstrated with aqueous solutions comprising very different antibodies and over a broad range of polysorbate 20 concentrations tested. These data clearly demonstrate that non-ionic surfactants such as Triton® X-100 are useful as additives that may be employed in protein-containing feed streams for reducing or preventing fouling of ultrafiltration membranes during the ultrafiltration process.

Example 3: The Effect of Prefiltration in Combination with Addition of Surfactant on Ultrafiltration Membrane Performance In another set of experiments, the effect of prefiltration in combination with surfactant addition on the rate of fouling of an ultrafiltration membrane was investigated. Specifically, the anti-PDL1 and anti-VEGF antibody-containing aqueous solutions described in Table 1 above were optionally treated with a surfactant and then subjected to prefiltration through a Mustang S® cation exchange membrane (Pall Corporation). Subsequent to prefiltration through the Mustang S® cation exchange membrane, the filtrate/surfactant solution was subjected to ultrafiltration as described above. The data obtained from these experiments are shown in FIGS. 8 and 9.

Figure 1:
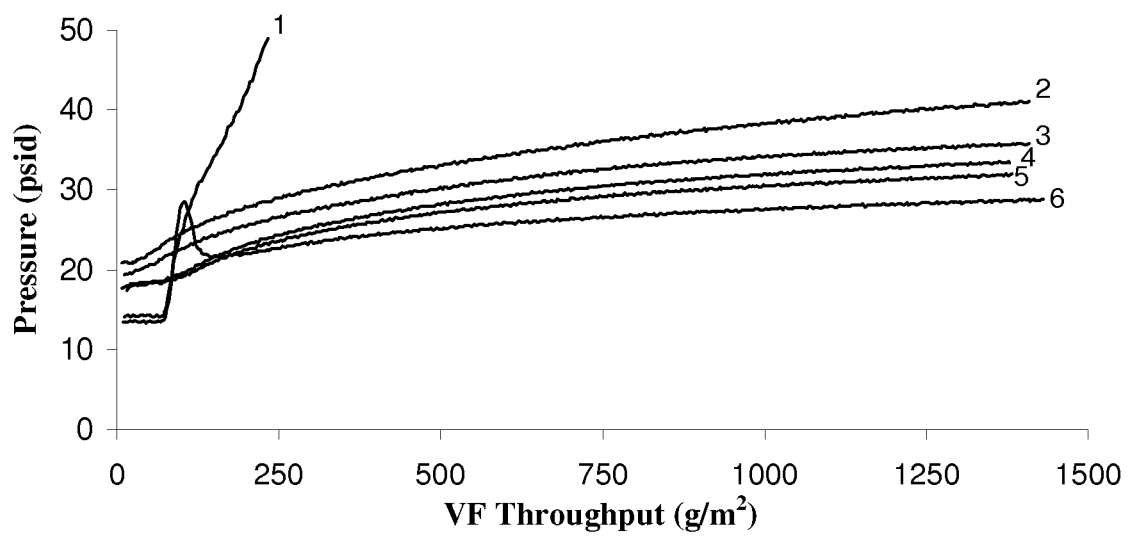
FIG. 1 shows the effect of polysorbate 20 on ultrafiltration of an aqueous solution comprising an anti-PDL1 antibody. Polysorbate 20 was added to the aqueous, antibody-containing feed stream at 0 ppm (1), 20 ppm (2), 50 ppm (3), 70 ppm (4), 100 ppm (5) and 1000 ppm (6). The throughput of the ultrafiltration membrane (VF) in $g/m^2$ is plotted against the transmembrane pressure in pounds per square inch
Figure 2:
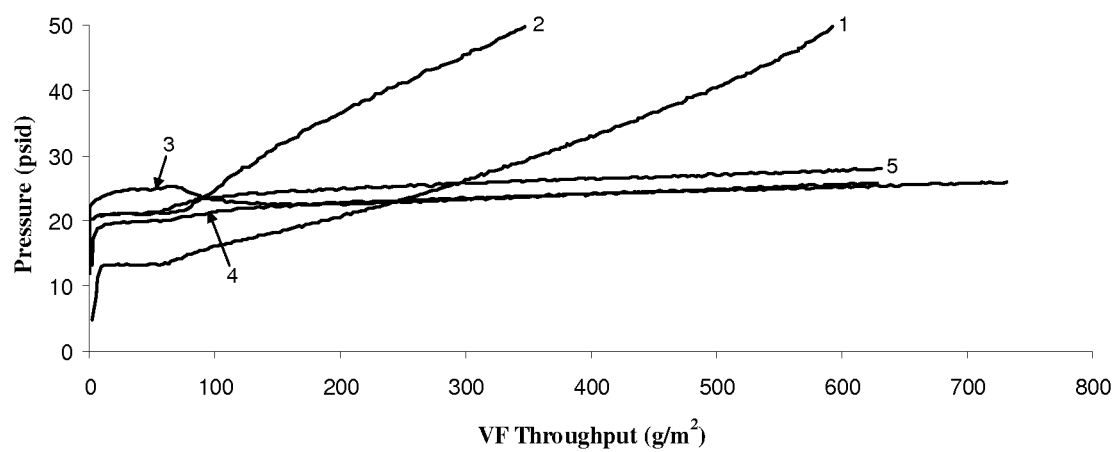
FIG. 2 shows the effect of polysorbate 20 on ultrafiltration of an aqueous solution comprising an anti-VEGF antibody. Polysorbate 20 was added to the aqueous, antibody-containing feed stream at 0 ppm (1), 20 ppm (2), 100 ppm (3), 1000 ppm (4), and 10,000 ppm (5). The throughput of the ultrafiltration membrane (VF) in $g/m^2$ is plotted against the transmembrane pressure in pounds per square inch.
Figure 3:
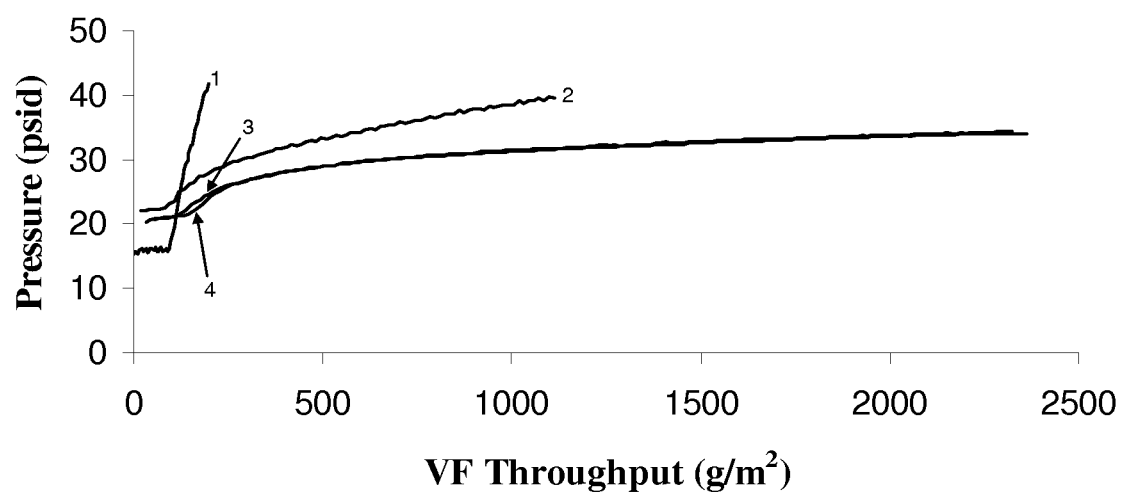
FIG. 3 shows the effect of polysorbate 20 on ultrafiltration of an aqueous solution comprising an anti-MUC16 antibody. Polysorbate 20 was added to the aqueous, antibody-containing feed stream at 0 ppm (1), 20 ppm (2), 100 ppm (3) and 1000 ppm (4). The throughput of the ultrafiltration membrane (VF) in $g/m^2$ is plotted against the transmembrane pressure in pounds per square inch.
Figure 4:
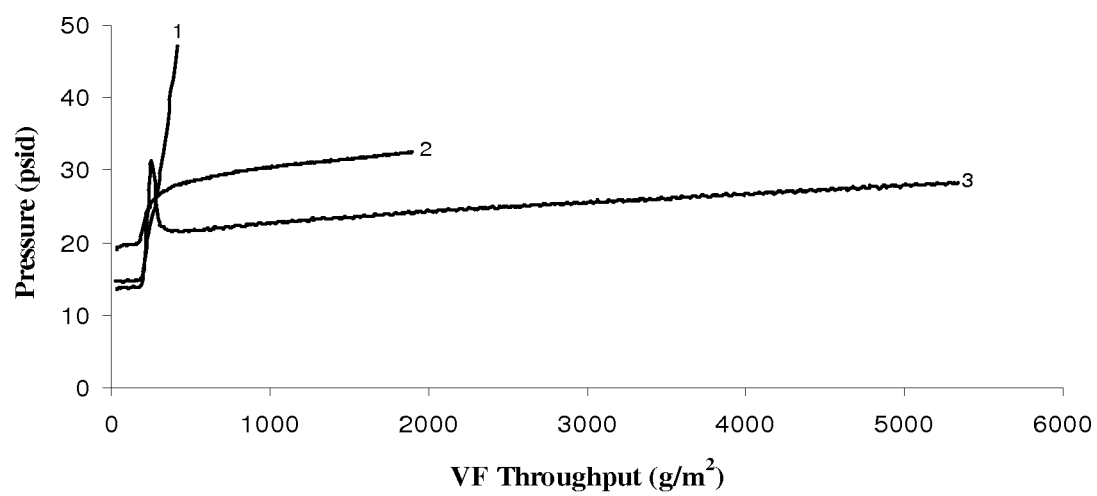
FIG. 4 shows the effect of no additive (1), 1000 ppm polysorbate 20 (2) or 1000 ppm Triton® X-100 (3) on ultrafiltration of an aqueous solution comprising an anti-DR5 antibody. The throughput of the ultrafiltration membrane (VF) in $g/m^2$ is plotted against the transmembrane pressure in pounds per square inch.
Figure 5:
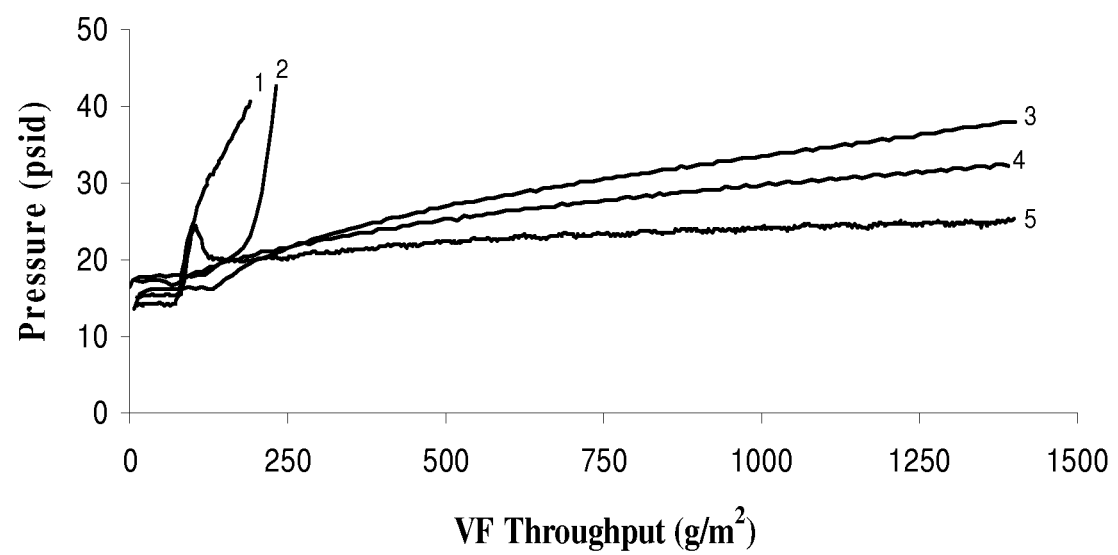
FIG. 5 shows the effect of Triton® X-100 on ultrafiltration of an aqueous solution comprising an anti-PDL1 antibody. Triton® X-100 was added to the aqueous, antibody-containing feed stream at 0 ppm (1), 20 ppm (2), 200 ppm (3), 300 ppm (4), and 1000 ppm (5). The throughput of the ultrafiltration membrane (VF) in $g/m^2$ is plotted against the transmembrane pressure in pounds per square inch.
Figure 6:
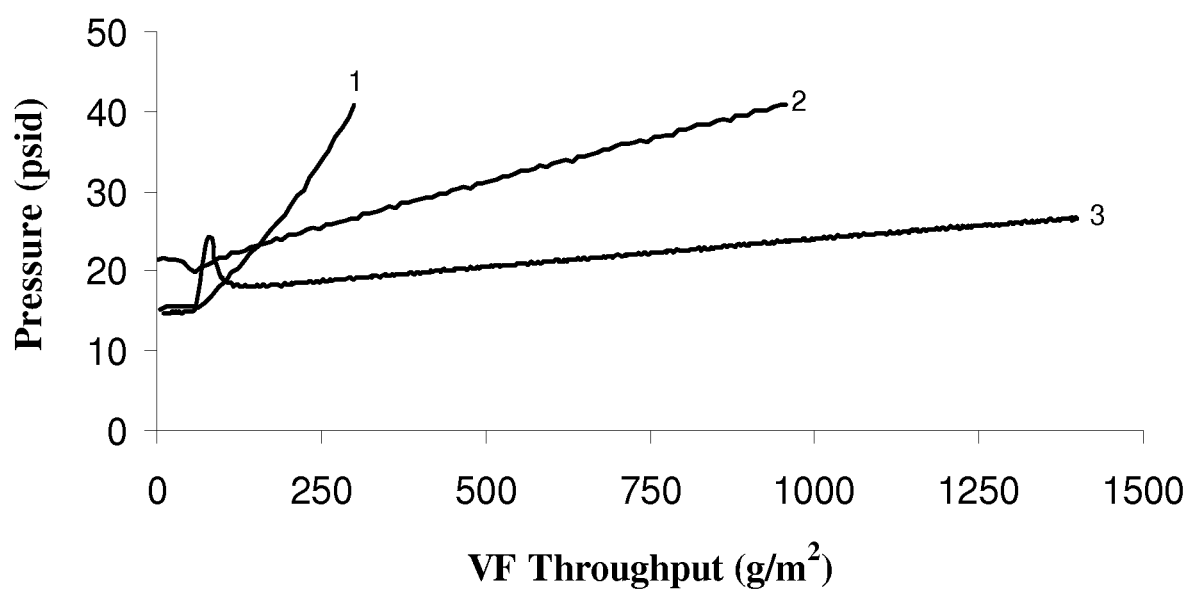
FIG. 6 shows the effect of Triton® X-100 on ultrafiltration of an aqueous solution comprising an anti-VEGF antibody. Triton® X-100 was added to the aqueous, antibody-containing feed stream at 0 ppm (1), 300 ppm (2), and 1000 ppm (3). The throughput of the ultrafiltration membrane (VF) in $g/m^2$ is plotted against the transmembrane pressure in pounds per square inch.
Figure 7:
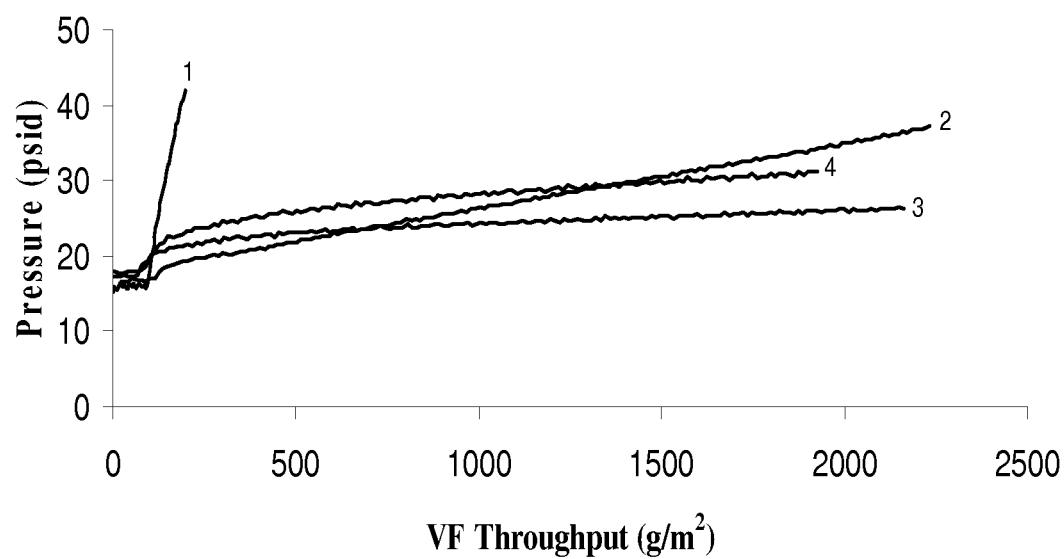
FIG. 7 shows the effect of Triton® X-100 on ultrafiltration of an aqueous solution comprising an anti-MUC16 antibody. Triton® X-100 was added to the aqueous, antibody-containing feed stream at 0 ppm (1), 150 ppm (2), 1000 ppm (3), and 2000 ppm (4). The throughput of the ultrafiltration membrane (VF) in $g/m^2$ is plotted against the transmembrane pressure in pounds per square inch.
Figure 8:
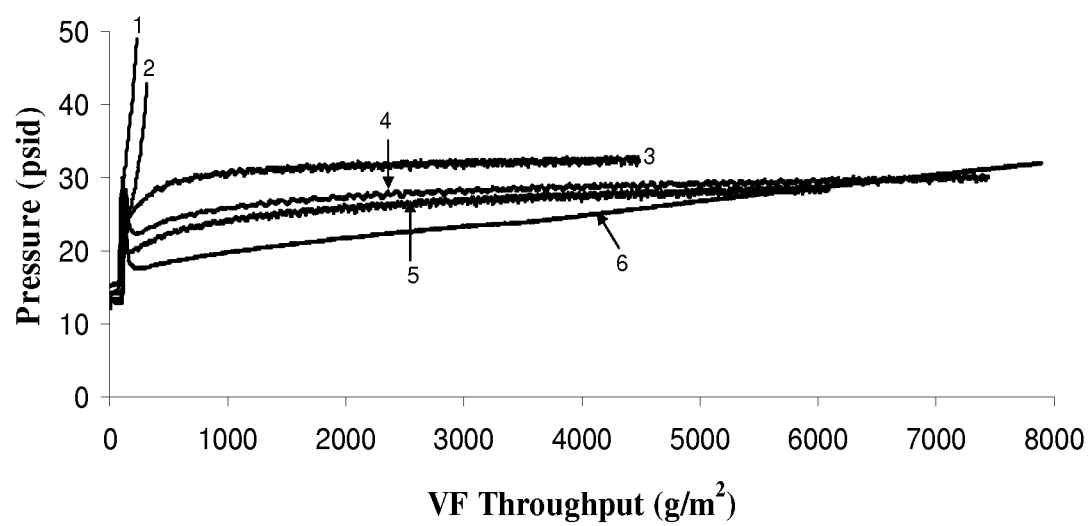
FIG. 8 shows the effect of polysorbate 20 or Triton® X-100, without or in combination with a prior prefiltration step, on ultrafiltration of an aqueous solution comprising an anti-PDL1 antibody. The following were investigated, no surfactant or prefiltration step (1), prefiltration using a Mustang S® cation exchange prefilter (2), 1000 ppm polysorbate 20 (3), prefiltration with a Mustang S® cation exchange prefilter plus 1000 ppm polysorbate 20 (4), 1000 ppm Triton® X-100 (5), and prefiltration with a Mustang S® cation exchange prefilter plus 1000 ppm Triton® X-100 (6). The throughput of the ultrafiltration membrane (VF) in $g/m^2$ is plotted against the transmembrane pressure in pounds per square inch.
Figure 9:
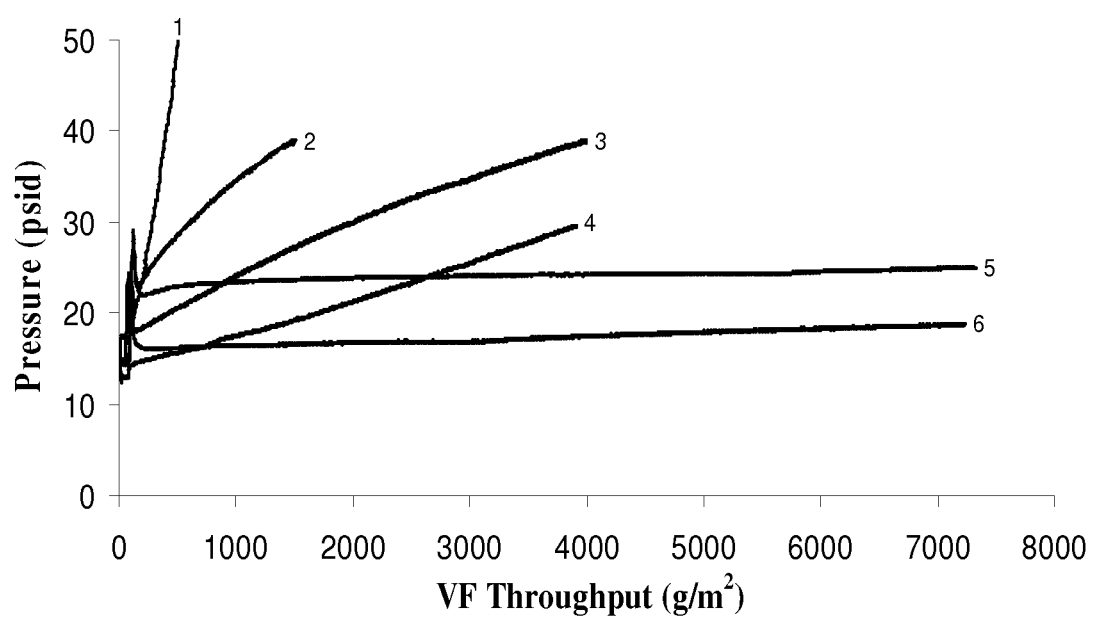
FIG. 9 shows the effect of polysorbate 20 or Triton® X-100, without or in combination with a prior prefiltration step, on ultrafiltration of an aqueous solution comprising an anti-VEGF antibody. The following were investigated, no surfactant or prefiltration step (1), 1000 ppm polysorbate 20 (2), 1000 ppm Triton® X-100 (3), prefiltration using a Mustang S® cation exchange prefilter (4), prefiltration with a Mustang S® cation exchange prefilter plus 1000 ppm polysorbate 20 (5), and prefiltration with a Mustang S® cation exchange prefilter plus 1000 ppm Triton® X-100 (6).

As shown in FIGS. 8 and 9, simple filtration through the Mustang S® has little or no beneficial effect on the prevention or reduction of fouling of a downstream ultrafiltration membrane. In contrast, however, when prefiltration of the aqueous antibody-containing solution was combined with the addition of a non-ionic surfactant, a strong reduction in fouling of a downstream ultrafiltration membrane was observed. These data clearly demonstrate that the use of an upstream prefiltration step in combination with surfactant addition provides a strong, reproducible and beneficial effect for reducing or preventing the fouling of a downstream ultrafiltration membrane in an ultrafiltration process for protein-containing aqueous solutions.

Example 4: The Effect of Other Surfactants and Certain Non-Surfactant, Non-Ionic Agents on Ultrafiltration Membrane Performance In yet another set of experiments, the effect of various different surfactant, or non-surfactant, non-ionic additives on the rate of fouling of a downstream ultrafiltration membrane was investigated. More specifically, various different surfactant and non-surfactant, non-ionic agents were added to different antibody-containing aqueous solutions (as described in Table 1), the subjected to ultrafiltration through a Viresolve® Pro ultrafiltration membrane as described in Example 1 above. The data from these experiments are shown in FIGS. 10 and 11.

As shown in FIGS. 10 and 11, a significant reduction in the fouling of a downstream ultrafiltration membrane was observed with a variety of different surfactants and non-surfactant, non-ionic agents. Additional data generated with various antibody solution, additive, prefilter combinations are provided in Table 2.

TABLE 2

| Antibody | Excipient or Prefilter | Throughput in g/m² (Final Transmembrane Pressure Achieved) |
|---|---|---|
| Anti-PDL1 | None | 200 |
|  | Mustang ® S pre-filter | 320 |
|  | Triton ® X-100 | >6000 (28.0) |
|  | Polysorbate 20 | >6000 (29.5) |
|  | PEG6000 | 250 |
|  | Octylβ-D-glucopyranoside | 200 |
|  | L-Arginine HCl | 400 |
|  | Triton ® X-100 + Mustang ® S prefilter | >6000 (29.4) |
| Anti-DR5 | None | 400 |
|  | Triton ® X-100 | >5000 (27.8) |
|  | Polysorbate 20 | >1750 (32.8) |
| Anti-VEGF | None | 450 |
|  | Mustang ® S prefilter | 4000 |
|  | Triton ® X-100 | 4000 |
|  | Polysorbate 20 | 1500 |
|  | PEG6000 | 1200 |

TABLE 2-continued

| Antibody | Excipient or Prefilter | Throughput in g/m² (Final Transmembrane Pressure Achieved) |
|---|---|---|
|  | Octylβ-D-glucopyranoside | 800 |
|  | L-Arginine HCl | 300 |
|  | Triton ® X-100 + Mustang ® S prefilter | >7200 (18.3) |
|  | Polysorbate 20 + Mustang ® S pre-filter | >7200 (24.3) |
| Anti-HER2 | None | 500 |
|  | Mustang ® S pre-filter | >12500 (30.1) |
|  |  | >10000 (27.6) |
|  | Triton ® X-100 | 5000 |
|  | PS20 | 600 |
|  | Triton ® X-100 + Mustang ® S prefilter | >23000 (18.6) |
|  |  | >10000 (17.1) |
|  | PS 20 + Mustang ® S prefilter | >23000 (22.0) |
|  |  | >10000 (21.0) |

These data demonstrate that a wide variety of surfactants and certain non-surfactant, non-ionic agents are useful as additives to protein-containing aqueous solutions for the reduction and/or prevention of fouling of an ultrafiltration membrane during the ultrafiltration process. These surfactants and non-surfactant, non-ionic agents are useful either with or without incorporation of a prefiltration step prior to the subsequent ultrafiltration step.

Example 5: Polysorbate 20 has No Negative Impact on Viral Clearance

A study was performed to demonstrate that the addition of a surfactant directly to a protein feed stream did not negatively impact viral clearance by an ultrafiltration membranea parvovirus filter. The study was conducted as follows.

Virus Stocks

Murine Minute Virus (MMV) is a non-enveloped, single stranded DNA genome, parvovirus approximately 18-24 nm in size, which is highly resistant to chemical inactivation. MMV stock was purchased from BioReliance (Rockville, Md.).

Virus Filtration

Feedstocks with and without surfactant additives were spiked 1/100th by volume with MMV stock. The spiked feedstock was filtered through a 0.22 μm filter and Viresolve Pro. Virus titer was determined by Q-PCR after the 0.22 μm filter and Viresolve Pro pool.

Virus Quantification

The Q-PCR assay is previously described by Strauss et al., (2008) *Biotechnology and Bioengineering,* 102:168-175 and Zhan et al., (2002) *Biologicals,* 30:259-70. Modifications were made to the nuclease digestion step to optimize removal of residual free DNA. Samples are adjusted to pH 8-9 and subjected to microccocal nuclease enzyme digestion for 30 minutes at 37° C. Extraction of viral genomic DNA was then performed using EZ1 Advanced XL with EZ1 virus mini kit v2.0 (Qiagen Inc., Valencia, Calif.). Q-PCR reaction was then performed as previously described.

Virus Clearance

Virus clearance is expressed as log reduction value (LRV). LRV were calculated as:

$$LRV = \log_{10} \times (\text{total virus in load/total virus in filtrate pool})$$

The results are shown in Table 3 below.

TABLE 3

| Antibody | Surfactant | LRV |
|---|---|---|
| Anti-VEGF | 0 ppm polysorbate 20 | 4.05 |
| Anti-VEGF | 100 ppm polysorbate 20 | 4.55 |
| Anti-VEGF | 1000 ppm polysorbate 20 | 4.37 |
| Anti-PDL1 | 0 ppm polysorbate 20 | 4.30 |
| Anti-PDL1 | 100 ppm polysorbate 20 | 4.59 |
| Anti-PDL1 | 1000 ppm polysorbate 20 | 4.67 |

The results from these analyses demonstrate that addition of the polysorbate 20 surfactant to the protein-containing feedstream does not adversely impact the ability of an ultrafiltration membrane to remove virus from the feedstream.

Example 6: Effect of Pretreatment of Ultrafiltration Membrane with Surfactant

A study was conducted to compare the effects of adding a surfactant directly into a feed stream prior to ultrafiltration with the effect of pretreating the membrane with a surfactant prior to ultrafiltration. The protein feed stream of an aqueous solution of anti-VEGF antibody was prepared as shown in Table 1. The ultrafiltration membrane was a Viresolve® Pro membrane. In some cases, the Viresolve® Pro membrane was prepared by pretreating the membrane with polysorbate 20, by filtering 1000 ppm polysorbate 20 (dissolved in water) prior to the ultrafiltration step. In other cases, polysorbate 20 was added directly to the feed stream prior to ultrafiltration using a membrane that had not been pretreated with a surfactant. As a control, a third feed stream with no surfactants added, either directly to the feed stream or as a pretreatment of the membrane. The results from this analysis are shown in FIG. 12. The data in FIG. 12 demonstrates that the greatest throughput was observed for the case where polysorbate 20 was added directly to the feed stream of the anti-VEGF antibody. Conversely, pretreatment of the ultrafiltration membrane with polysorbate 20 resulted in throughputs that were below the throughputs obtained for the control sample. These data demonstrate that addition of a surfactant or other non-ionic, non-surfactant agent directly to the aqueous protein-containing feedstream, as compared to pretreating the ultrafiltration membrane with the same, has a significant beneficial effect on reducing or preventing fouling of the ultrafiltration membrane.

Example 7: Use of Surfactants to Dissociate Protein Aggregates in Aqueous Solutions A study was performed to evaluate the dissociation of protein aggregates by using a surfactant. Samples were prepared by adding 10% stock solution of either polysorbate 20 or Triton® X-100 into the aqueous anti-PDL1 solution described in Table 1 to reach the final excipient concentration of 1000 ppm. The aqueous solutions containing excipient were incubated at room temperature for 30 mins before analysis. Aggregate particles ≥1.6 μm in the aqueous solution were measured using a HIAC (Liquid particle counting system, model 9703). The instrument was calibrated using PSL particle dispersion standards of known sizes ranging from 1.5 μm to 100 μm. The samples were gently mixed by swirling the container to homogeneously disperse the particles immediately before analysis. Four runs (1 mL for each run) of the aqueous samples were tested individually, and the particle numbers at designated sizes were counted. The data of the particle counts for the last three runs were recorded, while the result of the first run was discarded. Results from this analysis are shown in Table 4 below, where the numerical values represent the number of particles of the referenced size per ml of aqueous solution.

TABLE 4

| Particle Size (μm) | No surfactant | Polysorbate 20 | Triton ® X-100 |
|---|---|---|---|
| 1.6 | 103267 ± 5612 | 21433 ± 2479 | 14333 ± 1617 |
| 2.0 | 57967 ± 4823 | 13567 ± 1193 | 9500 ± 1054 |
| 5.0 | 11567 ± 1387 | 2967 ± 208 | 2633 ± 666 |
| 10.0 | 3800 ± 436 | 600 ± 300 | 800 ± 100 |
| 25.0 | 333 ± 115 | 67 ± 115 | 67 ± 58 |

As shown in Table 4, the HIAC data shows that the addition of surfactant in an antibody-containing aqueous feed solution can dissociate pre-existing aggregate particles and may, therefore, function to improve ultrafiltration membrane performance by reducing or preventing the fouling thereof.

What is claimed is:

1. A method of reducing fouling of an ultrafiltration membrane in a process wherein virus particles are removed from an aqueous solution comprising said virus particles and at least one protein, the method comprising the steps of
    a) adding to said aqueous solution a non-ionic surfactant wherein said non-ionic surfactant is selected from the group consisting of polysorbate 20, t-octylphenoxypolyethoxyethanol, polyoxyethylene (40) isooctylphenyl ether, and lauromacrogol; and
    b) filtering said aqueous solution comprising surfactant through said ultrafiltration membrane, wherein the presence of said surfactant in said aqueous solution reduces fouling of said ultrafiltration membrane; and wherein said step of filtering said aqueous solution is by normal flow filtration wherein viral particles are retained by the ultrafiltration membrane and the protein passes through the ultrafiltration membrane.

2. The method of claim 1, wherein said surfactant is polysorbate 20.

3. The method of claim 1, wherein said surfactant is added to said aqueous solution at a concentration of 1-10,000 PPM.

4. The method of claim 1, wherein said surfactant is added to said aqueous solution at a concentration of 10-200 PPM.

5. The method of claim 1, wherein said ultrafiltration membrane is a parvovirus retentive membrane.

6. The method of claim 1, wherein said ultrafiltration membrane has a pore size of less than about 100 nm or less.

7. The method of claim 1, wherein said ultrafiltration membrane has a pore size of about 20 nm or less.

8. The method of claim 1, wherein said protein is an antibody.

9. The method of claim 8, wherein said antibody is a monoclonal or humanized antibody.

10. The method of claim 9, wherein the monoclonal or humanized antibody is an anti-VEGF, an anti-PDL1, anti-HER2, anti-DR5, or an anti-MUC16.

11. The method of claim 1, wherein the addition of said surfactant to said aqueous solution enhances the filtration throughput efficiency of said ultrafiltration membrane by at least 10%.

12. The method of claim 1, wherein the addition of said surfactant to said aqueous solution enhances the filtration throughput efficiency of said ultrafiltration membrane by at least 50%.

13. The method of claim 1, wherein said virus particles are parvovirus particles.

14. The method of claim 1, further comprising the step of filtering said aqueous solution through one or more layers of adsorptive depth filters or one or more layers of charged or surface modified microporous membranes, prior to the filtration of said aqueous solution through said ultrafiltration membrane.

15. A method of enhancing filtration throughput efficiency of a ultrafiltration membrane in a process wherein virus particles are removed from an aqueous solution comprising said virus particles and at least one protein, the method comprising adding a non-ionic surfactant to said aqueous solution before filtering said aqueous solution through said ultrafiltration membranes, wherein the presence of said surfactant in said aqueous solution enhances the filtration throughput efficiency of said ultrafiltration membrane as compared to in the absence of said surfactant; wherein said non-ionic surfactant is selected from the group consisting of polysorbate 20, t-octylphenoxypolyethoxyethanol, polyoxyethylene (40) isooctylphenyl ether, and lauromacrogol; and wherein said step of filtering said aqueous solution is by normal flow filtration and wherein viral particles are retained by the ultrafiltration membrane and the protein passes through the ultrafiltration membrane.

16. The method of claim 15, wherein said surfactant is polysorbate 20.

17. The method of claim 15, wherein said surfactant is added to said aqueous solution at a concentration of 1-10,000 PPM.

18. The method of claim 15, wherein said surfactant is added to said aqueous solution at a concentration of 10-200 PPM.

19. The method of claim 15, wherein said ultrafiltration membrane is a parvovirus retentive membrane.

20. The method of claim 15, wherein said ultrafiltration membrane has a pore size of less than about 100 nm or less.

21. The method of claim 15, wherein said ultrafiltration membrane has a pore size of about 20 nm or less.

22. The method of claim 15, wherein said protein is an antibody.

23. The method of claim 22, wherein said antibody is a monoclonal or humanized antibody.

24. The method of claim 23, wherein the monoclonal or humanized antibody is an anti-VEGF, an anti-PDL1, anti-HER2, anti-DR5, or an anti-MUC16.

25. The method of claim 15, wherein the addition of said surfactant to said aqueous solution enhances the filtration throughput efficiency of said ultrafiltration membrane by at least 10%.

26. The method of claim 15, wherein the addition of said surfactant to said aqueous solution enhances the filtration throughput efficiency of said ultrafiltration membrane by at least 50%.

27. The method of claim 15, wherein said virus particles are parvovirus particles.

28. The method of claim 15, further comprising the step of filtering said aqueous solution through one or more layers of adsorptive depth filters or one or more layers of charged or surface modified microporous membranes, prior to the filtration of said aqueous solution through said ultrafiltration membrane.

29. A method to dissociate polypeptide aggregates or reduce the formation of polypeptide aggregates in a normal flow ultrafiltration feed stream comprising an aqueous solution comprising at least one protein, the method comprising adding a non-ionic surfactant to said aqueous solution, wherein said non-ionic surfactant is selected from the group consisting of polysorbate 20, t-octylphenoxypolyethoxyethanol, polyoxyethylene (40) isooctylphenyl ether, and lauromacrogol and filtering said aqueous solution comprising said non-ionic surfactant through a ultrafiltration membrane, wherein said step of filtering said aqueous solution is by normal flow filtration, wherein viral particles are retained by the ultrafiltration membrane and the protein passes through the ultrafiltration membrane, and wherein said dissociation of polypeptide aggregates or reduction in the formation of protein aggregates reduces fouling of the ultrafiltration membrane.

30. The method of claim 29, wherein said surfactant is polysorbate 20.

31. The method of claim 29, wherein said surfactant is added to said aqueous solution at a concentration of 1-10,000 PPM.

32. The method of claim 29, wherein said surfactant is added to said aqueous solution at a concentration of 10-200 PPM.

33. The method of claim 29, wherein said ultrafiltration membrane is a parvovirus retentive membrane.

34. The method of claim 29, wherein said ultrafiltration membrane has a pore size of less than about 100 nm or less.

35. The method of claim 29, wherein said ultrafiltration membrane has a pore size of about 20 nm or less.

36. The method of claim 29, wherein the addition of said surfactant to said aqueous solution enhances the filtration throughput efficiency of said ultrafiltration membrane by at least 10%.

37. The method of claim 29, wherein the addition of said surfactant to said aqueous solution enhances the filtration throughput efficiency of said ultrafiltration membrane by at least 50%.

38. The method of claim 29, further comprising the step of filtering said aqueous solution through one or more layers of adsorptive depth filters or one or more layers of charged or surface modified microporous membranes, prior to the filtration of said aqueous solution through said ultrafiltration membrane.

39. The method of claim 29, wherein said protein is an antibody.

40. The method of claim 39, wherein said antibody is a monoclonal or humanized antibody.

41. The method of claim 40, wherein the monoclonal or humanized antibody is an anti-VEGF, an anti-PDL1, anti-HER2, anti-DR5, or an anti-MUC16.

42. A method of reducing fouling of a ultrafiltration membrane in a process wherein virus particles are removed from an aqueous solution comprising said virus particles and at least one protein, the method comprising the steps of
  a) filtering said aqueous solution through a device selected from the group consisting of one or more layers of adsorptive depth filters and one or more layers of charged or surface modified microporous membranes;
  b) adding a non-ionic surfactant to said aqueous solution, wherein said non-ionic surfactant is selected from the group consisting of polysorbate 20, t-octylphenoxypolyethoxyethanol, polyoxyethylene (40) isooctylphenyl ether, and lauromacrogol; and
  c) filtering said aqueous solution comprising said surfactant through said ultrafiltration membranes, wherein the presence of said surfactant in said aqueous solution reduces fouling of said ultrafiltration membrane, wherein said step of filtering said aqueous solution is by normal flow filtration and wherein viral particles are retained by the ultrafiltration membrane and the protein passes through the ultrafiltration membrane.

43. The method of claim 42, wherein said surfactant is polysorbate 20.

44. The method of claim 42, wherein said surfactant is added to said aqueous solution at a concentration of 1-10,000 PPM.

45. The method of claim 42, wherein said surfactant is added to said aqueous solution at a concentration of 10-200 PPM.

46. The method of claim 42, wherein said ultrafiltration membrane is a parvovirus retentive membrane.

47. The method of claim 42, wherein said ultrafiltration membrane has a pore size of less than about 100 nm or less.

48. The method of claim 42, wherein said ultrafiltration membrane has a pore size of about 20 nm or less.

49. The method of claim 42, wherein said protein is an antibody.

50. The method of claim 49, wherein said antibody is a monoclonal or humanized antibody.

51. The method of claim 50, wherein the monoclonal or humanized antibody is an anti-VEGF, an anti-PDL1, anti-HER2, anti-DR5, or an anti-MUC16.

52. The method of claim 42, wherein the addition of said surfactant to said aqueous solution enhances the filtration throughput efficiency of said ultrafiltration membrane by at least 10%.

53. The method of claim 42, wherein the addition of said surfactant to said aqueous solution enhances the filtration throughput efficiency of said ultrafiltration membrane by at least 50%.

54. The method of claim 42, wherein said virus particles are parvovirus particles.

55. A method of reducing fouling of a ultrafiltration membrane in a process wherein virus particles are removed from an aqueous solution comprising said virus particles and at least one protein, the method comprising the steps of
a) adding a non-ionic surfactant to said aqueous solution, wherein said non-ionic surfactant is selected from the group consisting of polysorbate 20, t-octylphenoxy-polyethoxyethanol, polyoxyethylene (40) isooctylphenyl ether, and lauromacrogol,
b) filtering said aqueous solution through a device selected from the group consisting of one or more layers of adsorptive depth filters and one or more layers of charged or surface modified microporous membranes; and
c) filtering said aqueous solution comprising said surfactant, wherein the presence of said surfactant in said aqueous solution reduces fouling of said ultrafiltration membrane, wherein said step of filtering said aqueous solution is by normal flow filtration and wherein viral particles are retained by the ultrafiltration membrane and the protein passes through the ultrafiltration membrane.

56. A method of reducing fouling of a ultrafiltration membrane in a process wherein virus particles are removed from an aqueous solution comprising an antibody, the method comprising the steps of
a) adding to said aqueous solution a non-ionic surfactant wherein said non-ionic surfactant is selected from the group consisting of polysorbate 20, t-octylphenoxy-polyethoxyethanol, polyoxyethylene (40) isooctylphenyl ether, and lauromacrogol; and
b) filtering said aqueous solution comprising said surfactant through said ultrafiltration membranes, wherein the ultrafiltration membrane has a pore size of less than about 100 nm or less, wherein the presence of said surfactant in said aqueous solution reduces fouling of said ultrafiltration membrane; and wherein said step of filtering said aqueous solution is by normal flow filtration and wherein viral particles are retained by the ultrafiltration membrane and the protein passes through the ultrafiltration membrane.

57. The method of claim 56, wherein said surfactant is polysorbate 20.

58. The method of claim 56, wherein said surfactant is added to said aqueous solution at a concentration of 1-10,000 PPM.

59. The method of claim 56, wherein said ultrafiltration membrane has a pore size of about 20 nm or less.

60. The method of claim 56, wherein said antibody is a monoclonal or humanized antibody.

61. The method of claim 60, wherein the monoclonal or humanized antibody is an anti-VEGF, an anti-PDL1, anti-HER2, anti-DR5, or an anti-MUC16.

62. The method of claim 56, wherein said virus particles are parvovirus particles.

\* \* \* \* \*

UNITED STATES PATENT AND TRADEMARK OFFICE
CERTIFICATE OF CORRECTION

PATENT NO. : 10,906,934 B2
APPLICATION NO. : 14/007610
DATED : February 2, 2021
INVENTOR(S) : Arick Brown et al.

Page 1 of 1

It is certified that error appears in the above-identified patent and that said Letters Patent is hereby corrected as shown below:

In the Claims
At Column 30, Claim number 10, Line numbers 58-59, please replace "anti-HER2, anti-DR5" with --an anti-HER2, an anti-DR5--.
At Column 31, Claim number 15, Line number 15, please replace "membranes" with --membrane--.
At Column 31, Claim number 24, Line numbers 45-46, please replace "anti-HER2, anti-DR5" with --an anti-HER2, an anti-DR5--.
At Column 32, Claim number 29, Line number 5, please replace "a ultrafiltration" with --an ultrafiltration--.
At Column 32, Claim number 41, Line numbers 46-47, please replace "anti-HER2, anti-DR5" with --an anti-HER2, an anti-DR5--.
At Column 32, Claim number 42, Line number 48, please replace "a ultrafiltration" with --an ultrafiltration--.
At Column 32, Claim number 42, Line number 63, please replace "membranes" with --membrane--.
At Column 33, Claim number 51, Line numbers 22-23, please replace "anti-HER2, anti-DR5" with --an anti-HER2, an anti-DR5--.
At Column 33, Claim number 55, Line number 34, please replace "a ultrafiltration" with --an ultrafiltration--.
At Column 34, Claim number 56, Line number 11, please replace "a ultrafiltration" with --an ultrafiltration--.
At Column 34, Claim number 56, Line number 21, please replace "membranes" with --membrane--.
At Column 34, Claim number 61, Line numbers 40-41, please replace "anti-HER2, anti-DR5" with --an anti-HER2, an anti-DR5--.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*